US011950316B1

(12) United States Patent
Nalevanko et al.

(10) Patent No.: US 11,950,316 B1
(45) Date of Patent: Apr. 2, 2024

(54) VEHICLE-PASSENGER ASSISTANCE FACILITATION

(71) Applicant: Zoox, Inc., Foster City, CA (US)

(72) Inventors: Christopher Robert Nalevanko, Menlo Park, CA (US); Riccardo Giraldi, San Francisco, CA (US); Amanda Brown Prescott, Austin, TX (US)

(73) Assignee: Zoox, Inc., Foster City, CA (US)

( * ) Notice: Subject to any disclaimer, the term of this patent is extended or adjusted under 35 U.S.C. 154(b) by 125 days.

(21) Appl. No.: 17/525,809

(22) Filed: Nov. 12, 2021

(51) Int. Cl.
| | | |
|---|---|---|
| *H04W 76/50* | (2018.01) | |
| *A61B 5/00* | (2006.01) | |
| *B60W 40/08* | (2012.01) | |
| *B60W 60/00* | (2020.01) | |
| *G07C 5/00* | (2006.01) | |
| *G07C 5/08* | (2006.01) | |
| *H04W 4/02* | (2018.01) | |
| *H04W 4/40* | (2018.01) | |
| *H04W 4/90* | (2018.01) | |

(52) U.S. Cl.
CPC .......... *H04W 76/50* (2018.02); *A61B 5/0002* (2013.01); *B60W 40/08* (2013.01); *B60W 60/0016* (2020.02); *G07C 5/008* (2013.01); *G07C 5/0808* (2013.01); *H04W 4/025* (2013.01); *H04W 4/40* (2018.02); *H04W 4/90* (2018.02); *B60W 2540/221* (2020.02); *B60W 2556/45* (2020.02)

(58) Field of Classification Search
CPC ...................................................... H04W 76/50
USPC ...................................................... 455/404.2
See application file for complete search history.

(56) References Cited

U.S. PATENT DOCUMENTS

| | | | | |
|---|---|---|---|---|
| 10,414,377 | B2 * | 9/2019 | Hoyos | ................ H04L 63/0861 |
| 11,562,550 | B1 * | 1/2023 | Asghar | ................... G06T 19/20 |
| 2015/0061895 | A1 | 3/2015 | Ricci | |
| 2018/0348759 | A1 * | 12/2018 | Freeman | ............. A61N 1/3904 |
| 2020/0255002 | A1 | 8/2020 | Chen | |
| 2021/0366266 | A1 * | 11/2021 | Owens | ................... H04L 65/40 |

OTHER PUBLICATIONS

Office Action for U.S. Appl. No. 17/525,800, dated Nov. 8, 2023, Christopher Robert Nalevanko, "Vehicle-Event Application Notifications", 13 pages.

* cited by examiner

*Primary Examiner* — Qutbuddin Ghulamali
(74) *Attorney, Agent, or Firm* — Lee & Hayes, P.C.

(57) ABSTRACT

Vehicles may be associated with a variety of different types of events, including events associated with vehicle operations and/or events associated with vehicle passengers. The present disclosure is related to, when an event is detected, exchanging information with a vehicle passenger, such as via the passenger's mobile device and/or wearable device. In some instances, an event may be detected, and examples of the present disclosure may provide an application notification presenting various information. The notification may, in some examples, be configured to help the passenger locate the passenger device, to alert the passenger to the event, to provide instructions, and/or to provide a control interface for controlling a vehicle operation. In some examples, the notification may supersede operations of the passenger device, such as by being presented even if the device is in a locked state or has an unrelated application open and in the foreground.

20 Claims, 6 Drawing Sheets

VEHICLE-PASSENGER ASSISTANCE FACILITATION

BACKGROUND

Vehicles may be associated with a variety of different events. Some events may relate to the operations of the vehicle. For example, a vehicle may be involved in a collision event and/or may detect a component-failure event, either of which may limit vehicle operations. In addition, some events may relate to a passenger of a vehicle, such as when a passenger experiences a health event (e.g., elevated heart rate or other unexpected vital signs) or an altercation between passengers of the vehicle. In some instances, when an event occurs, it may be challenging to exchange information with a vehicle passenger, such as information notifying the passenger of the event, information instructing the passenger regarding steps to be taken, and/or information that could help facilitate assistance for the passenger.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

FIGS. 1A, 1B, and 1C depict respective scenarios or events that might be associated with the vehicle.

DETAILED DESCRIPTION

Figure 1A:
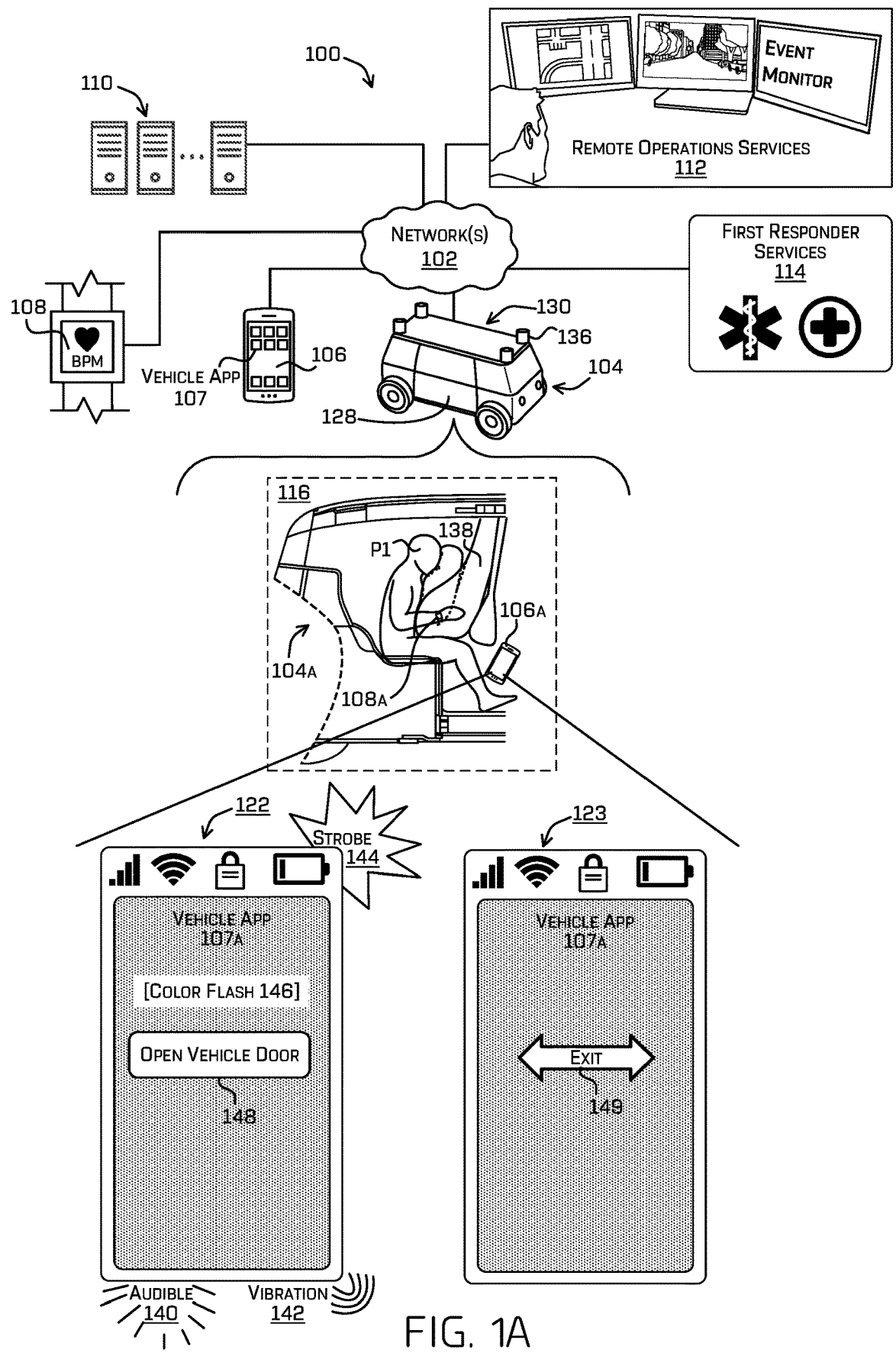
FIGS. 1A, 1B, and 1C depict an example system, including a vehicle associated, via a network, with various components, in accordance with one or more examples of this disclosure.

As discussed above, vehicles may be associated with a variety of different types of events, including events associated with vehicle operations and/or events associated with vehicle passengers. The present disclosure is related to, when an event is detected, exchanging (e.g., sending and/or receiving) information with a vehicle passenger, such as via the passenger's mobile device and/or wearable device ("passenger devices"). For example, in some instances, an event may be detected, and examples of the present disclosure may provide an application notification (e.g., via the passenger devices) presenting various information. The notification may, in some examples, be configured to help the passenger locate the passenger device, to alert the passenger to the event, to provide instructions, and/or to provide a control interface for controlling a vehicle operation (e.g., open a vehicle door, select a different route/destination, call first responder services, etc.). In some examples, to mitigate risks associated with passenger disorientation or to aid in locating a mobile device, the notification may be conspicuous (e.g., large, bright, flashing, etc.) and/or supersede operations of the passenger device (e.g., be presented even if the device is in a locked state or has an unrelated application open and in the foreground). In these respects, examples of the present disclosure may, among other things, increase the likelihood that, when an event occurs, a passenger is able to locate their passenger device and be alerted to valuable information. In some examples, when an event is detected, information associated with the passenger (e.g., vital signs, emergency contact details, etc.) may be obtained from the passenger device(s) or other, and in some cases, may be provided to first responder services and/or other third parties. As such, examples of the present disclosure may, when an event is detected, increase the likelihood that information is provided to parties who may be able to assist with the event.

Having described some general examples of the present disclosure, some more specific examples are now described. As mentioned, a vehicle may sometimes be involved in a collision, which may be detected by various components. For example, in some instances a collision event may be detected based on sensor data associated with a collision-detection system, an airbag sensor, a microphone, a body deformation sensor, a brake sensor, a steering sensor, a motion sensor (e.g., IMU), a perception sensor (e.g., camera, lidar, radar, sonar, etc.), or any combination thereof. In some examples, a collision event may be detected based on sensor data meeting a threshold (e.g., braking rate, deceleration rate, steering rate, distance to a detected object, etc.). In some examples, a collision event may be detected based on an operational state (e.g., limited operational state) detected with respect to a component of the vehicle. In some examples, a collision event may be detected based on a motion of a passenger device (e.g., sudden acceleration and/or deceleration detected by a passenger-device IMU). In examples, a collision event can be detected via sensor characterization (e.g., determining an audio profile that corresponds to a collision).

Various operations may be performed in connection with detecting a collision event. In some examples, a severity associated with the event may be assessed. For example, the severity may be based on the extent to which vehicle operations may be limited, such as whether the vehicle is still fully operational (e.g., the collision was only minor), whether airbags were deployed, whether one or more systems of the vehicle have been damaged (e.g., body damage, steering alignment, etc.), and/or based on sensor data from one or more sensors of the vehicle (e.g., an IMU of the vehicle, a microphone of the vehicle, etc.). In some examples, a severity associated with the event may be based on information associated with the passenger device(s) (e.g., accelerations detected by the passenger-device IMU, elevated heart rate or other irregular vital signs received from a wearable device of the user, etc.). In examples, a level of displacement likely imparted to the user or the user's device may be used to determine whether certain features of the disclosed techniques are activated, such as generating an especially conspicuous notification.

In at least some examples, based on the collision event, an application notification may be provided via a passenger device. For example, in some instances, an application may have been previously downloaded to the passenger device, and the application may be configured to facilitate interaction between the passenger and the vehicle and/or a vehicle operator. For example, via the application, the passenger may be able to request a ride, specify a destination, provide payment details, and the like. In addition, in some examples, via the application, a passenger may be able to control vehicle operations, such as by changing a route or destination, operating a door (e.g., opening and/or closing), selecting entertainment options, changing cabin conditions, and the like. In some examples, via the application, a passenger may be able to exchange information with a remote operator (e.g., a person remotely located away from the vehicle and able to control vehicle operations). In accordance with examples of the disclosure, the application may, based on the collision, present a notification via the passenger device.

The application notification may be configured for various purposes, goals, intents, etc. For example, the notification may be configured to assist a passenger with locating the passenger device, such as when the passenger device has been dispossessed from the passenger due to the collision or when the passenger device is concealed in a bag or other location. Stated differently, absent examples provided in this disclosure, in some events a passenger may lose possession of their passenger device and/or otherwise be unable to locate their passenger device (e.g., due to disorientation, view blocked by deployed airbag, etc.). However, some examples of the present disclosure may assist a passenger with finding their phone by presenting a notification configured to alert a passenger to the phone's whereabouts (e.g., conspicuous full-screen notifications, audible, haptic, and/or visible elements). In some examples, the notification may be configured to provide information to the passenger describing and/or otherwise related to the event. In some examples, the notification may be configured to provide a description of one or more steps to follow. In some examples, the notification may provide one or more interface controls for a passenger to use to control an operation of the vehicle, such as an interface control to open a door of the vehicle or change a route/destination of the vehicle. That is, as explained above, the application may provide interface controls that enable a passenger to control vehicle operations, such as opening a vehicle door, releasing a restraint system (e.g., seatbelt), etc. Absent examples described in this disclosure, in some collision events, a passenger may have difficulty quickly navigating to the interface control within the application. As such, some examples of the present disclosure may provide an interface element for opening a door as an element of the application notification, which may increase the likelihood that the passenger is able to open the door quickly and exit the vehicle, thereby increasing safety associated with the vehicle.

The application notification may include various elements, including various visual elements (e.g., on-screen notification, flashing or strobe effect, etc.), audible elements (e.g., alarm, audible instructions, etc.), haptic elements (e.g., vibration), and the like. Any of these elements may be configured based on one or more contexts. For example, any of these elements may be configured based on an event type and/or severity. In addition, any of these elements may be configured based on passenger-specific context information (e.g., sensory disability, preferred language, passenger-specific notification preferences, etc.). In at least some examples, the notification may be presented regardless of a state of the mobile device, such as regardless of whether the mobile device is in a locked state or has an unrelated application (or no application) open and in the foreground. In some examples, the notification may supersede other display functionality of the mobile device. In some examples, any of these elements may be configured based on a position and/or orientation of the passenger device relative to the passenger and/or to the vehicle. For example, a first type of notification may be provided when the passenger device is determined to be facing the passenger (e.g., passenger is holding device and viewing device and/or providing input to device), whereas a second type of notification may be provided when the passenger device is determined to be not facing the passenger. As another example, a third type of notification may be provided when the passenger device is determined to be in possession of the passenger (e.g., in a hand, pocket, or bag of the user), whereas a fourth type of notification may be provided when the passenger device is determined to not be in possession of the passenger (e.g., on the floor, under a seat, etc.). As such, examples of the present disclosure are configured to convey information with an amount or magnitude of sensory input (e.g., volume, brightness, etc.) less likely to unnecessarily overwhelm the passenger. In some examples, elements and/or content of a notification may be configured based on a state of a passenger, such as whether a passenger is experiencing a potential altercation with another passenger or current health state (e.g., asleep, fall, stroke, heart attack, etc.). In examples, the mobile device may enter a state wherein a subset of functionality may be presented to a user to aid the user in response to the event. This state may be configured to enable a user (possibly not the mobile device's owner) to quickly access the functionality without requiring the user to enter a password, fingerprint, etc. The limited functionality may pertain to providing instructions, enabling certain controls for the vehicle, and/or communication functionality to emergency services as further disclosed herein.

The application notification may be presented based on various other conditions or criteria. In some examples, timing associated with the application notification may be based on whether a threshold duration has passed after a threshold event. For example, the vehicle may include a door control for opening and closing the vehicle door, and a presentation of the notification may be based on whether a time duration has elapsed between a collision event and use of the door control to open the vehicle door. In some examples, the notification may change (e.g., presentation escalation) after a threshold duration has passed from an initial presentation and no passenger feedback has been received.

As described above, in some examples of the present disclosure, the application (e.g., executing on the passenger device(s)) may receive information associated with the passenger (e.g., medical information, vital signs, emergency contact information, etc.). The information may be received under various contexts. For instance, in some examples, the application may receive, in connection with a collision event, information that is associated with the passenger and that may be provided to one or more entities possibly able to assist with the collision event and/or the passenger. In some examples, the application may receive, independent of any collision event, information that is associated with the passenger and that may indicate a health anomaly, altercation with another passenger, or other distress event. This information can include information self-reported by a user, accessed from a medical database, and/or determined using sensors of a smart device, such as a wearable.

Various operations (e.g., of the vehicle, of the application, etc.) may be based on (e.g., triggered by) the information received by the application, such as where the information satisfies a condition. In some examples, an application notification may be presented based on the information. For instance, the notification may alert the user that an irregular health condition was detected, alert the user that a potential altercation with another passenger was detected, provide options for the passenger to communicate with a contact (e.g., emergency contact, first responder service, etc.), request feedback from the passenger regarding a status of the passenger, automatically prompt an incoming call from a service (e.g., remote operations services or first responder services), and the like. In some examples, based on the information received by the application, a communication channel may be established, such that the passenger is able to communicate with another party (e.g., first responder service, remote vehicle operations, emergency contact, etc.). The information may, in some examples, be provided to one or more entities that may be able to assist the passenger. In some examples, a location of the vehicle and/or the passenger device may be provided to the one or more entities. In some examples, operations of the vehicle may be based on the information received by the passenger device(s). For example, based on a health anomaly, a trajectory of the vehicle may be modified to include a different destination, such as a first responder service, a healthcare facility, or an emergency-stop location. Among other things, examples of the present disclosure may increase a likelihood that a health condition is detected earlier and/or may enable responsive action to be taken sooner by alerting other parties, changing a vehicle trajectory, alerting the passenger, and the like.

The techniques described herein can be implemented in a number of ways to provide event-based notifications and/or to initiate various measures based on information received from a passenger device. Examples are provided below with reference to FIGS. 1A, 1B, 1C, 2, and 3. Examples are discussed in the context of autonomous vehicles; however, the methods, apparatuses, and components described herein can be applied to a variety of components (e.g., other robotic applications), and are not limited to autonomous vehicles. In one example, the techniques described herein may be utilized in driver-controlled vehicles, vessels, aircrafts, or other passenger transports. Furthermore, the techniques described herein can be used with real data (e.g., captured using sensor(s)), simulated data (e.g., generated by a simulator), or any combination of the two.

Figure 1B:
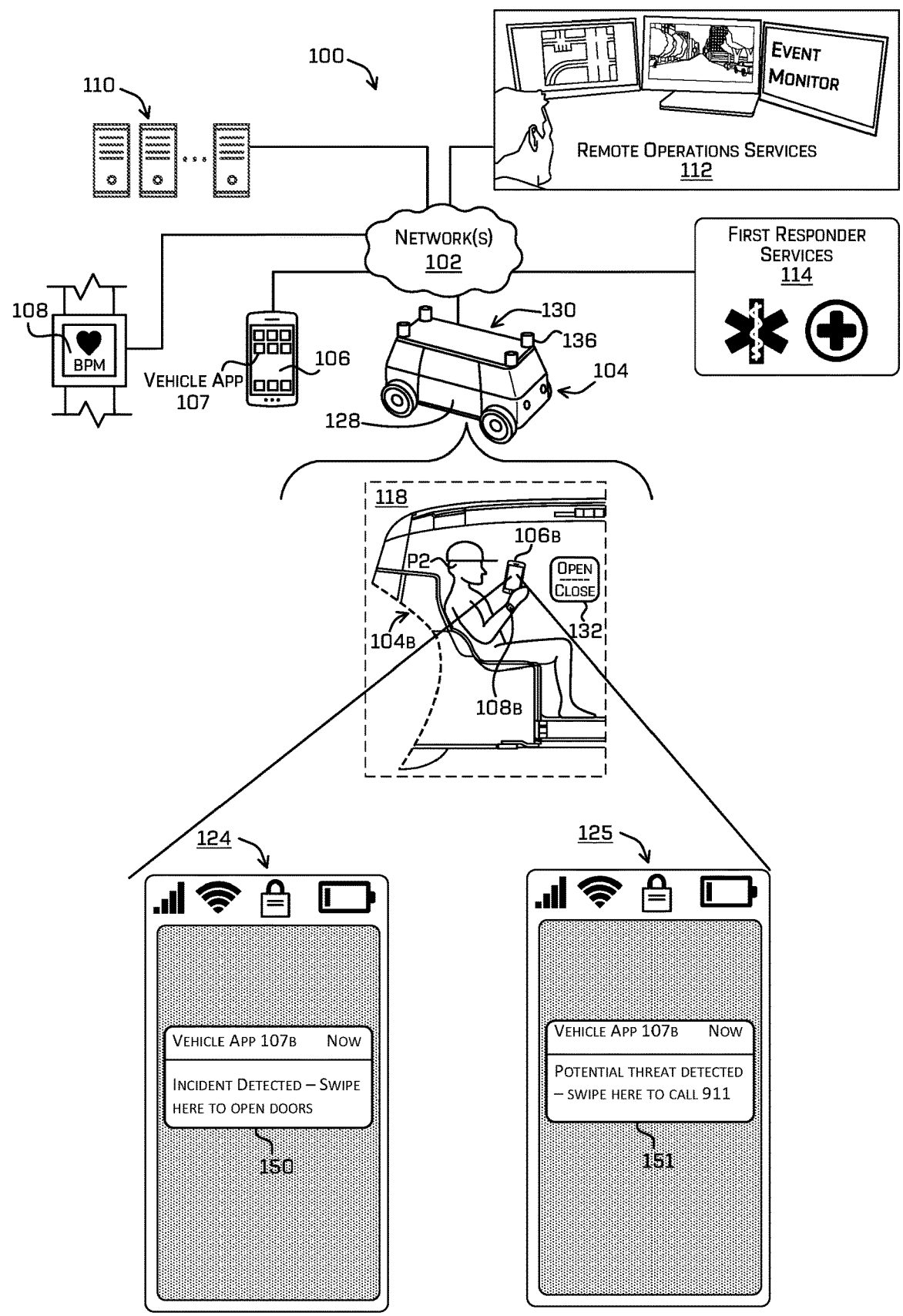
Figure 1C:
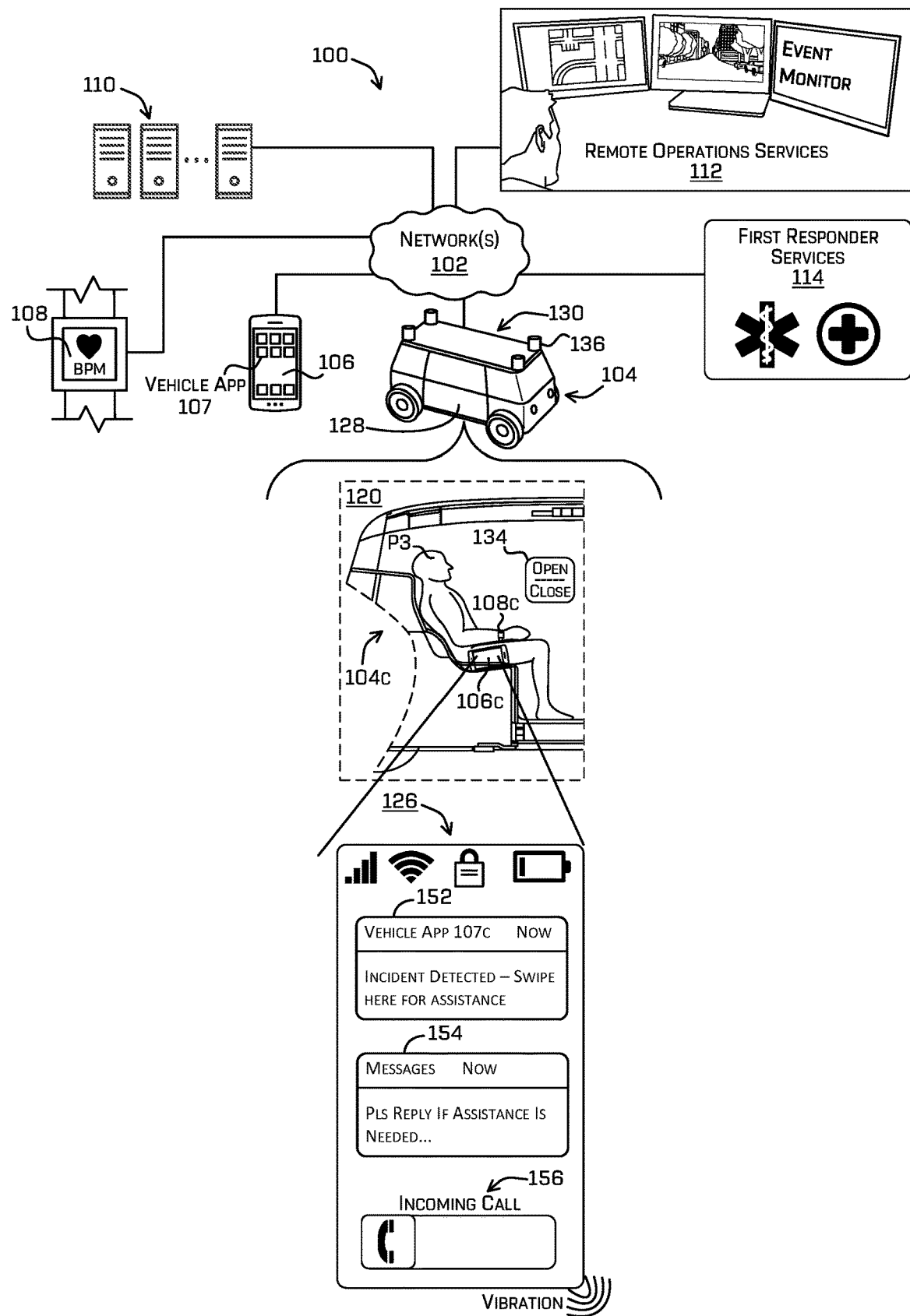

Referring to FIGS. 1A, 1B, and 1C, a system 100 of networked components are depicted that may exchange various data and information in association with an event (e.g., collision, health anomaly, passenger altercation, emergency, passenger egress scenario, etc.). FIGS. 1A, 1B, and 1C are depicted to include a similar system 100, but each depicts a respective scenario or event that might be associated with a vehicle, as well as example application notifications that might be presented in association with the scenarios or events. In examples, the system 100 includes a network 102 (e.g., at least one network) communicatively connecting a vehicle 104, a passenger mobile device 106, a passenger wearable device 108, computing device(s) 110 (e.g., onboard and/or offboard), remote operations services 112, and first responder services 114. The network(s) 102 may include one or more of a variety of different networks facilitating wired and/or wireless communication (e.g., WIFI, Bluetooth, cellular, ethernet, satellite communication, dedicated short-range communications (DSRC), or any suitable wired or wireless communications protocol that enables the respective computing device to interface with the other computing device(s)).

In one example, the vehicle 104 is a bidirectional vehicle having a first drive module positioned in a front end and a second drive module positioned in a rear end. As used herein, a bidirectional vehicle is one that is configured to switch between traveling in a first direction of the vehicle and a second, opposite, direction of the vehicle. In other words, there is no fixed "front" or "rear" of the vehicle 104. Rather, whichever longitudinal end of the vehicle 104 is leading at the time becomes the "front" and the trailing longitudinal end becomes the "rear." In addition, the vehicle 104 may include doors (e.g. sliding doors) on both sides 128 and 130 of the vehicle 104. In some examples, the vehicle 104 may include an in-vehicle door control (e.g., in-vehicle door control 132 in FIG. 1B and in-vehicle door control 134 in FIG. 1C) associated with each door (e.g., affixed to an interior wall of the vehicle) that may be used (e.g., by pressing a button or switch or selecting an interface element on a touch-screen enabled device) to operate the door. In other examples, the techniques described herein may be applied to vehicles other than bidirectional vehicles. Also, whether or not the vehicle is bidirectional, the first drive and second drive modules may be different from one another. In addition, the vehicle 104 may include sensors (e.g., 136), any of which may include a perception sensor, including a sensor capturing data of an environment around the vehicle 104 (e.g., lidar, camera, time-of-flight, sonar, radar, etc.). The vehicle 104 may include a variety of other sensors used to assess a condition of vehicle systems or sub-systems, such as the braking, steering, drive, power, suspension, safety (e.g., airbags), collision-detection sensors, body-damage sensors, and the like. In some examples, the vehicle 104 may include any elements described with respect to the vehicle 302 in FIG. 3.

The computing devices 110 may include onboard computing devices (e.g., present with the vehicle 104) and/or offboard computing devices that may be remote from the vehicle 104. In examples, the computing devices 110 include processors and memory for performing operations described herein and/or in connection with vehicle operation. In some examples, the computing devices 110 include any of the elements described with respect to the computing devices 304 or 344 of FIG. 3.

The remote operations services 112 may receive information from the vehicle 104 (e.g., location data, sensor data, perception data, etc.) and may provide guidance and information to the vehicle 104 to assist the vehicle 104 with various operations. For example, the remote operations services 112 and the vehicle 104 may include one or more examples described in U.S. Pat. No. 10,386,836, entitled "Interactions Between Vehicle and Teleoperations System," which is incorporated by reference herein in its entirety for all intents and purposes. In some examples, the vehicle 104 and/or the remote operations services 112 may include components for assisting a passenger when an event is detected (e.g., collision even, vehicle systems or sub-systems faults, emergency health event, etc.). For example, based on the event, the vehicle 104 and the remote operations services 112 may establish a communication channel to exchange information, communicate with the passenger, etc. In addition, as described in more detail in other portions of this disclosure, the remote operations services 112 may receive information (e.g., related to event(s)) associated with the mobile device 106 and/or the wearable device 108 and may send information to the mobile device 106 and/or the wearable device 108. As used herein, the term "device" may describe a computing device or an application running on the computing device. In examples, the solutions that include connecting to the passenger's mobile device 106 may provide a backup safety system to assist the passenger when an event is detected.

The first responder services 114 may include one or more entities providing first responder services. For example, the first responder services may include EMT services, paramedics, firefighters, ambulatory services, police officers, and the like. In some examples, the first responder services 114 may respond to, or otherwise assist with, events detected in association with the vehicle 104 and/or passengers of the vehicle 104.

Often, a passenger of the vehicle 104 has their own mobile device, such as the mobile device 106, and/or a wearable device 108. In examples of the present disclosure, the mobile device 106 may include a mobile phone, smart phone, tablet, or other mobile computing device (e.g., other type of mobile computing device, wearable computing device (e.g., smart watch), personal computing device, etc.). In addition, the wearable device 108 may include a watch, ring, chest strap, wrist strap, implanted device, or other device worn, secured, or otherwise coupled to the passenger. The wearable device 108 may, among other things, monitor conditions associated with the passenger, such as body temperature, heart rate, breathing rate, VO2, blood chemistry (e.g., glucose), other vital signs, etc. In some examples, the wearable device 108 need not be a device that is physically worn by the user, and in some instances, the wearable device 108 may be a second computing device (e.g., either worn or not worn) associated with the passenger. In examples, the mobile device 106 and the wearable device 108 may exchange information, such as (with the passenger's permission) the wearable device 108 providing data associated with the passenger to the mobile device 106.

In addition, the mobile device 106 may include an application (e.g., "vehicle app 107") configured to facilitate interaction between the passenger and the vehicle 104 and/or a vehicle-related operator. For example, using the application, the passenger may be able to request a ride, specify a destination, provide payment details, and the like. In addition, in some examples, using the application, a passenger may be able to control vehicle operations, such as by requesting a new destination, operating a door (e.g., opening and/or closing), selecting entertainment options, changing cabin conditions, and the like. Furthermore, in some examples, the application may (e.g., with the passenger's permission) exchange information with other computing devices, such as associated with the remote operations services 112, the first responder services 114, contacts, etc. For example, the application may provide, to other computing devices, information associated with the passenger, including information received from the wearable device 108 (e.g., with the passenger's permission).

Examples of the present disclosure include, when an event is detected, exchanging (e.g., sending and/or receiving) information with a vehicle passenger, such as via the mobile device 106 and/or the wearable device 108. For example, in some instances, an event may be detected, and examples of the present disclosure may provide, via the vehicle app 107, a notification presenting various information. The notification may, in some examples, be configured to help the passenger locate the mobile device 106, to alert the passenger to the event, to provide instructions, and/or to provide a control interface for controlling a vehicle operation (e.g., open a vehicle door, select a different route, call first responder services, etc.). In some examples, when an event is detected, information associated with the passenger (e.g., vital signs, emergency contact details, etc.) may be obtained (e.g., with the passenger's permission) via the mobile device 106 and/or wearable device 108, and in some cases, may be provided to first responder services and/or other parties. As such, examples of the present disclosure may, when an event is detected, increase the likelihood that information is provided to parties who may be able to assist with the event, which may increase safety associated with the vehicle.

FIGS. 1A, 1B, and 1C illustrate scenarios 116, 118, and 120 in which, based on an event, various operations may be executed. Each of the scenarios 116, 118, and 120 depicts a passenger P1, P2, and P3 that is associated with (e.g., riding in) a vehicle 104a, 104b, and 104c (may collectively be referred to as the vehicle(s) 104). In addition, each passenger P1, P2, and P3 is associated with a mobile device 106a, 106b, and 106c, any of which may be similar to the mobile device 106. The mobile devices 106a, 106b, and 106c are associated with respective notifications 122, 123, 124, 125, and 126 provided by the vehicle app 107a, 107b, and 107c (respectively, which may be similar to the vehicle app 107). As explained above, the notifications 122, 123, 124, 125, and 126 may depend on various factors, such as the type of event (e.g., collision event, health event, passenger altercation, destination arrival, other distress, etc.); the severity of the event; a state of the mobile device 106 (e.g., in-hand, pocket, bag, dispossessed, unlocked and open, locked, etc.); a location of the mobile device relative to the passenger and/or vehicle; and the like. A severity of the event may be based on one or more various criterion, including whether airbags were deployed, whether a motion or operation of the vehicle satisfies a vehicle-motion threshold (e.g., braking rate, steering rate, rate of directional change, etc.), whether operations of the vehicle (e.g., one or more systems of the vehicle) are limited, whether a motion sensed by the mobile device exceeds a threshold (e.g., device-motion threshold), health data associated with the passenger (e.g., vital signs, biometrics, etc.), other vehicle sensor data satisfying a threshold (e.g., sound threshold), and the like.

As mentioned, the vehicle(s) 104 may sometimes be involved in a collision, which may be detected by various components. For example, a collision may be detected by the vehicle (e.g., by sensor(s) of the vehicle(s) 104), which may notify the application 107, and/or the mobile device 106 may detect the collision (e.g., based on sensors of the mobile device 106). Various operations may be performed in connection with detecting a collision event. In accordance with examples of the disclosure, the application 107 may, based on the collision, present a notification via the mobile device 106. The application notification may be configured for various purposes, goals, intents, etc. For example, the notification may be configured to assist a passenger with locating the mobile device 106, such as when the mobile device 106 has been dispossessed from the passenger due to the collision or when the mobile device 106 is concealed in a bag or other location. In addition, the notification may be configured to assist a passenger with navigating through steps following a collision (e.g., opening a door, communicating with remote operations services, communicating with first responder services, etc.). In some instances, the notification may include graphically presented instructions and/or audibly presented instructions. In some examples, the notification may include user interface (UI) elements configured to receive feedback or input from a passenger and perform a corresponding action or operation. In some examples, the mobile device 106 may automatically open a communication channel with a teleoperator, paramedic, or other remotely located responder. The communication channel may be opened in response to a request by a remotely located responder when a requisite event is detected.

Referring to the scenario 116, the vehicle 104a has experienced a collision in which an airbag 138 has been deployed and the mobile device 106a is dispossessed from the passenger P1. In examples of the disclosure, the application 107a may, based on the collision event, present the notification 122, including a full-screen takeover notification (or other conspicuous notification) to alert the passenger P1 to the mobile device 106a whereabouts and to assist the passenger P1 with finding the mobile device 106a. In some examples, the notification 122 may be presented on a lock screen, home screen, or application screen presented by the mobile device 106*a*. That is, the notification may be presented regardless of a state of the mobile device, such as regardless of whether the mobile device is in a locked state, has an unrelated application (or no application) open and in the foreground, and/or the application 107*a* is closed and/or in the background. In this sense, the notification may effectively take over the mobile device. In some examples, the presentation of the notification may supersede other display functionality of the mobile device.

The form of the notification 122 may be based on various factors, including whether airbags were deployed, motion detected by the mobile device 106*a*, motion detected by the vehicle 104, limited operational states detected by the vehicle 104, whether the mobile device 106*a* is facing the passenger P1, whether the mobile device 106*a* is unlocked, whether the mobile device 106*a* is locked, whether the vehicle app 107*a* is running in the background (e.g., having been recently used to request a ride), notification permissions granted by the passenger (e.g., permission to present on lock screen, to supersede other mobile-device functions, etc.), and the like. In addition to occupying the screen of the mobile device 106*a*, the notification 122 may include various other elements intended to assist the passenger P1 with finding the mobile device 106*a*. For example, the notification 122 may also or alternatively present an audible alert 140 (e.g., alarm, chime, spoken instructions/explanation, etc.), haptic vibrations 142, strobe 144 or other illumination, and/or screen-color changes or flashes 146. As such, examples of the present disclosure may assist a passenger with locating their mobile device in a scenario in which the mobile device is obscured from the passenger's view and/or the passenger is otherwise disoriented.

The notification 122 may include other elements as well. For example, the notification 122 may include a door control interface 148 that, when selected, operates a door of the vehicle 104*a* (e.g., performs a door-opening operation). The door control interface 148 may provide a redundant or backup control that can be used in lieu of a dedicated door control, such as the door control 132/134 (obscured from view by the airbag 138 in the scenario 116). The door control interface 148 (or other vehicle-related control) may be presented at various times and in combination with various notification elements. For example, in some cases, the door control interface 148 may be presented together with other elements configured to aid the passenger P1 with locating their device. In some examples, the door control interface 148 may be presented after the mobile device 106*a* receives input indicating the passenger P1 has located their phone. For instance, the mobile device 106*a* may receive an input silencing one or more elements of the notification 122, and based on the input, the door-control interface 148 may be presented. In some instances, the door control interface 148 may be presented in response to input indicating the passenger P1 is picking up the mobile device 106*a* and/or turning over the mobile device 106*a* over (e.g., to look at the screen). In some examples, the door control interface 148 may be presented after a determination that an egress path from the vehicle is clear (e.g., lower likelihood of risks to the passenger, such as traffic, smoke inhalation, etc.).

In addition, the door control interface 148 may assist the passenger P1 with steps to follow (e.g., open the door) when a collision event is detected. The steps may be tailored depending on a state of the vehicle or user. For example, if it is determined that the vehicle is located in a heavily trafficked area (such as in the middle of a highway) and/or that there is no immediate danger to the user (e.g., minimal risk of smoke inhalation), the user may be directed to stay in the vehicle until a responder can arrive. Alternatively, if a dangerous condition within the vehicle is detected, the user may be instructed to exit the vehicle and instruction s provided accordingly to allow the user to safely and expeditiously exit the vehicle. The instructions to exit the vehicle may also be tailored based on a condition of the vehicle and/or an environment of the vehicle. For example, a door may be damaged or blocked and therefore the user may be directed to a different, functioning door or other escape avenue.

In examples of the disclosure, the application 107*a* may, based on the collision event, present other notifications, such as the notification 123. In an example, the notification 123 includes an graphical icon arrow 149 that points (e.g., statically or animatedly, such as with motion pulses) in the direction of one or more doors of the vehicle (e.g., one or more open doors of the vehicle). For example, based on a location and orientation of the mobile device 106*a*, relative to the vehicle 104*a*, the arrow 149 may change the direction(s)(orientation) in which the arrow 149 is pointing, such that the arrow 149 is constantly pointing in the direction of the one or more doors. In some examples, the notification 123, or elements of the notification 123 may be presented after the door control interface 148 has been selected. In some examples, elements of the notification 123 may be presented together with elements of the notification 122. In some examples, the vehicle app 107*a* may transition from the notification 122 to the notification 123 by silencing one or more of the more conspicuous elements (e.g., haptic vibration, alarm, etc.) of the notification 122 (e.g., based on an input indicating the passenger P1 has located, or is in possession of, the device, such as a selection of the door control interface 148, motion detected by mobile device sensors, selection of a volume control, etc.). Among other things, the notification 123, including the arrow 149, may assist the passenger P1 with locating an exit of the vehicle, and may improve safety associated with the vehicle 104*a*. The arrow 149 may be directed based on an orientation of a mobile device through the use of internal Inertial Measurement Units (IMUs), external locating techniques (e.g., WiFi or millimeter wave trilateration, etc.).

Referring to FIG. 1B, FIG. 1B depicts the scenario 118 in which an event has been detected, and based on the event, severity, and/or other information a less conspicuous notification (as compared to the notification 122) may be more effective at accomplishing one or more intents or purposes of the notification. For example, the vehicle 104*b* may have been involved with a minor collision and automatically executed an emergency stop (but in the scenario 118, the passenger P2 is still in possession of and/or looking at their mobile device 106*b*), or a potential altercation of the passenger P2 may have been detected, in which case the passenger P2 may want to discretely request assistance.

In examples, the vehicle 104*b* may provide information to the vehicle app 107*b* indicating the minor collision and the emergency stop. In some examples, the vehicle app 107*b* may, based on the collision event, present the notification 124, including superseding other display functionality to alert the passenger P2 of the event and present a description of next steps to the passenger P2. In some examples, the notification 124 may be presented on a lock screen, home screen, or application screen presented by the mobile device 106*b*. The form of the notification 124 may be based on various factors. For example, the vehicle app 107*b* may determine (e.g., via native operations of the mobile device 106*b* or other applications on the mobile device 106*b*) that the mobile device 106*b* is facing the passenger and/or that the mobile device 106*b* has not been dispossessed (e.g., based on motion sensor data). In examples, the form of the notification may be based on whether the mobile device 106*b* is unlocked, whether the mobile device 106*b* is locked, whether the vehicle app 107*a* is running in the background (e.g., having been recently used to request a ride), notification permissions granted by the passenger (e.g., permission to present on lock screen, to supersede other mobile-device functions, etc.). The vehicle app 107*b* may also asses a severity level associated with the collision (e.g., based on airbag deployment (if any), motion detected by the mobile device 106*b* and/or the vehicle 104*b*, operational states detected by the vehicle 104*b*, etc.). In addition to occupying the screen of the mobile device 106*b*, the notification 124 may include various other elements intended to assist the passenger P2. For example, the notification 124 may present an interface element 150 (e.g., notification) providing a description of the event (e.g., "The vehicle was involved in a minor collision. A new vehicle is on it's way."). In addition, the interface element 150 may, if selected (e.g., swiped left), provide other interface elements, such as a door control interface element, option to call remote operations services 112, or options to control other vehicle operations (e.g., ramp operations, luggage release, suspension adjustments, restraint-system release, etc.). As such, examples of the present disclosure may increase a likelihood that a passenger is timely apprised of events and assist a passenger with event-related steps. In addition, examples may tailor the notification based on various factors, such as the severity of the event and whether the passenger is already looking at their mobile device.

In some examples, the vehicle 104*b* and/or remote operations services 112 may provide information to the mobile device 106*b* indicating another event (e.g., other than a collision), such as a medical emergency event, potential altercation (e.g., argument, fight, threatening behavior, etc. between the passenger P2 and another passenger in the vehicle), etc. For example, a medical emergency event may be detected based on information (e.g., current medical information) consumed from the wearable device 108*b* and/or medical information provided by an app on the mobile device 106*b*. In some examples, a potential altercation may be detected based on sensor data (e.g., image data from a camera, audio data from a microphone, etc.) associated with the vehicle 104*b*. In some examples, based on the indication of the potential alteration, the vehicle app 107*b* may present a notification 125 alerting the passenger P2 that an event or threat has been detected, and providing the passenger P2 with a mechanism to request assistance (e.g., control usable to communicate with a first responder, police, etc.). For example, in response to a selection (e.g., swipe) of the notification 125, an interface element 151 may be provided to enable the passenger P2 to initiate a phone call (or select some other user interface element) requesting assistance. In one example, requesting assistance may include a mechanism to allow the passenger P2 to request an emergency stop, request a route change, and/or request first responder assistance.

The notifications 122 and 124 that are based on collision events may also be based on various other conditions or criteria. In some examples, timing associated with the notifications 122 and 124 may be based on whether a threshold duration has passed after the collision is detected. For example, a presentation of the notifications 122 and 124 may be based on whether a time duration has elapsed between a collision event and use of the door control (e.g., 134) to open the vehicle door. That is, in some examples, if the door control 134 is used within a threshold duration, then presentation of the notifications 122 and 124 may be suspended. In some examples, the notifications 122 and 124 may change (e.g., presentation escalation) after a threshold duration has passed from an initial presentation and no passenger feedback has been received. That is, the notifications 122 and 124 may be initially presented with an initial set of sensory inputs, the number and/or magnitude of which may be increased after elapse of a time duration with no feedback or response received from the passenger (e.g., dismissing the notification). In some examples, a format of the notifications 122 and 124 may be based on biometric data associated with the passenger (e.g., as obtained from a wearable device). For example, if the passenger is determined to be experiencing increased stress, the quantity and/or magnitude of sensory outputs may be reduced. In some examples, the notifications may silence or de-escalate after a threshold duration (e.g., timed out period), such that if the notification has not been silenced or otherwise responded to within some time period, presentation elements of the notification are turned off.

The notifications 122 and 124 are examples of some notifications that may be presented when a collision event is detected, and examples of the present disclosure may present other notifications in such instances. For example, in some cases, when a collision event is detected, a communication channel with the mobile device 106 may be established (e.g., a new channel that would not otherwise be available) without needing passenger initiation, and a notification (e.g., received text message, incoming phone call, outgoing phone call, etc.) may alert the passenger to the availability of the new communication channel. In some examples, the communication channel may communicatively connect the mobile device 106 with remote operations services 112 and/or first responder services 114. Among other things, the communication channel with the mobile device 106 may provide a redundant and/or backup channel, such as if a communication channel with the vehicle 104 is damaged (e.g., due to the collision) or otherwise unusable.

As described above, in some examples of the present disclosure, the application 107 may receive, under various contexts, information associated with the passenger (e.g., medical information, vital signs, emergency contact information, etc.). For instance, the application 107 may receive (e.g., from the wearable device 108 and with the passenger's permission, from a remote medical database, and/or via a health or medical app), in connection with a collision event. Referring to scenarios 116 and 118, the passengers P1 and P2 may be associated with a wearable device 108*a* and 108*b*, which may be similar to the wearable device 108. Various operations (e.g., of the vehicle, of the application, etc.) may be based on (e.g., triggered by) the information received by the application, such as where the information (e.g., vital signs) satisfies a condition. In some examples, based on the information received by the application 107*a* and 107*b*, a communication channel may be established (e.g., automatically connected), such that the passenger P1 and P2 is able to communicate with another party (e.g., first responder service, remote vehicle operations, emergency contact, etc.). In at least some examples, the information received (e.g., vital signs) may, with the passenger's permission, be provided to one or more entities (e.g., first responder services 114) that may be able to assist the passenger P1 and P2. In some examples, allergies, medical conditions, or other health information can be provided to first responders to aid in providing medical aid.

In some examples, the application 107 may receive (e.g., from the wearable device 108 and/or from another application on the device 106 synced to the wearable device 108), independent of a collision event, information that is associated with the passenger and that may indicate a health anomaly or other distress event. For example, referring to FIG. 1C including the scenario 120, the passenger P3 is depicted with the mobile device 106c (e.g., may be similar to the mobile deice 106) and with a wearable device 108c (e.g., may be similar to the wearable device 108). A vehicle application 107c (e.g., similar to the vehicle application 107) may be downloaded to the mobile device 106c. In examples, the vehicle application 107c may receive (e.g., with the passenger's permission) information (e.g., vital signs) from the wearable device 108c, and various operations may be based on the information, such as where the information satisfies a condition. Information from the wearable device 108c may indicate a "current medical condition," associated with the passenger (e.g., as the data is sensed in near real time and communicated to the mobile device 106c. In addition, the vehicle app 107c may receive data from another application on the mobile device 106c, the other application being synced with the wearable device 108c, and the data from the other application may indicate historical health information (e.g., health data previously captured by the wearable device 108c and provided to a synced application on the mobile device 106c).

In some examples, the application notification 126 may be presented (e.g., presented on the lock screen, home screen, and/or application screen) based on the information received from the wearable device 108c and/or an application synced to the wearable device, and the notification 126 may include one or more different types of indications. For instance, the notification 126 may include an indication 152 alerting the passenger P3 that an event (e.g., health event, such as an irregular heartbeat, heart attack, stroke, fall, unconsciousness, etc.) was detected and provide options for the passenger P3 to request assistance. In addition, the notification 126 may include a message indication 154, indicating that a communication channel has been established with a contact (e.g., emergency contact, first responder service, etc.) and is usable to request assistance by sending a reply message. In another example, the notification 126 may include an incoming call indication 156 (or alternatively an outgoing call indication), indicating that a communication channel has been established with a contact (e.g., emergency contact, first responder service, etc.) and is usable to request assistance. In some examples, based on the information received by the application 107c, a communication channel (e.g., associated with SMS messaging, with a phone call, video call, etc.) may be automatically established between the mobile device 106c and the remote operations services 112 and/or the first responder services 114. As such, examples of the present disclosure may provide a new channel that may not otherwise be available and/or that could provide a backup or redundant communication option.

In addition, as explained with respect to the scenarios 116 and 118, the information received from the wearable device 108c may, in some examples and with passenger permission, be provided to one or more entities that may be able to assist the passenger. In some examples, a location of the vehicle 104c and/or the mobile device 106c may also be provided to the one or more entities. In some examples, operations of the vehicle may be based on the information received by the passenger device(s). For example, based on a health anomaly, a trajectory of the vehicle may be modified to include a different destination, such as a first responder service, a healthcare facility, or an emergency-stop location. Among other things, examples of the present disclosure may increase a likelihood that a health condition is detected earlier and/or may enable responsive action to be taken sooner by alerting other parties, changing a vehicle trajectory, alerting the passenger, and the like. In some examples, patient identification information can be provided to responders, such as an image of the user, their name, etc.

The notifications 122, 123, 124, 125, and 126 are examples of some notifications, and in examples of the present disclosure, notifications may include a variety of other or alternative elements and intended purposes. In some examples, the notifications may be automatically generated based on operations of the vehicle app 107, such that the remote operations services 112 need not provide input to the vehicle 104 and/or to the vehicle app 107. In some examples, the remote operations services 112 may provide input to the vehicle 104 and/or to the vehicle app 107, and the notification may be provided based at least in part on the input from the remote operations services 112. For example, the remote operations services 112 may detect an event (e.g., based on sound recorded from a microphone of the vehicle, image recorded from a vehicle camera, etc.) and trigger a notification based on the event. In some examples, the mobile device 106 and/or the wearable device 108 may communicate and/or sync (e.g., via Bluetooth) with I/O components of the vehicle (e.g., display, speaker, etc.), such that information rendered via the mobile device 106 and/or the wearable device 108 (e.g., information associated with an event and/or notification) is rendered via the vehicle components.

The notifications 122 and 124, including interface elements that may be used to open a vehicle door, are described with respect to a collision event. In some examples, notifications with door control interface elements may be presented under any condition in which egress from the vehicle may be desired. For example, notifications with door control interface elements may be presented when a vehicle arrives at a planned destination, when a vehicle performs an emergency stop or otherwise prematurely stops before reaching a planned destination, when a vehicle detects limited vehicle operations (e.g., operations that are not performing as intended), or any combination thereof. In other examples, a notification including a door interface control element may be presented when a health anomaly or other medical emergency associated with the passenger is detected.

The scenarios 116, 118, and 120 are depicted to include a single passenger. In some examples, the vehicle 104 may include multiple passengers with multiple mobile devices that may receive notifications. In some examples, the notifications may be color-coded (e.g., based on a color associated with a passenger's seat in the vehicle), such that if multiple mobile devices are dispossessed, the color coding may help a passenger identify their device. In some examples, multiple notifications across multiple devices may be simultaneously presented and silencing one notification (e.g., by acknowledging or opening a door) may silence multiple of the notifications. In some examples, a distinctive (e.g., user selected) ringtone or other audio message may be emitted.

In examples (e.g., as described with respect to FIGS. 1A-1C), based on an event (e.g., collision, health event, altercation, etc.), a passenger is provided with a mechanism to call first responder services 114 (e.g., police, EMT, fire department, etc.). In some examples, based on the call mechanism, a communication channel is established providing a three-way communication channel between the passenger (e.g., via the mobile device 106 or vehicle 104), the first responder services 114, and the remote operations services 112). In some examples, the three-way communication channel may allow various event-related information (e.g., location of vehicle and passenger, health information, etc.) to be exchanged between the parties. In some examples, the call mechanism (e.g., to the first responder services) may also provide an indication to the remote operations services 112 to alert the remote operations services 112 to the fact that the call was made. In some examples, based on the call, the location of the vehicle 104 may be presented on a display of the vehicle 104 and/or a display of the mobile device 106 to notify the passenger of their current location.

Figure 2:
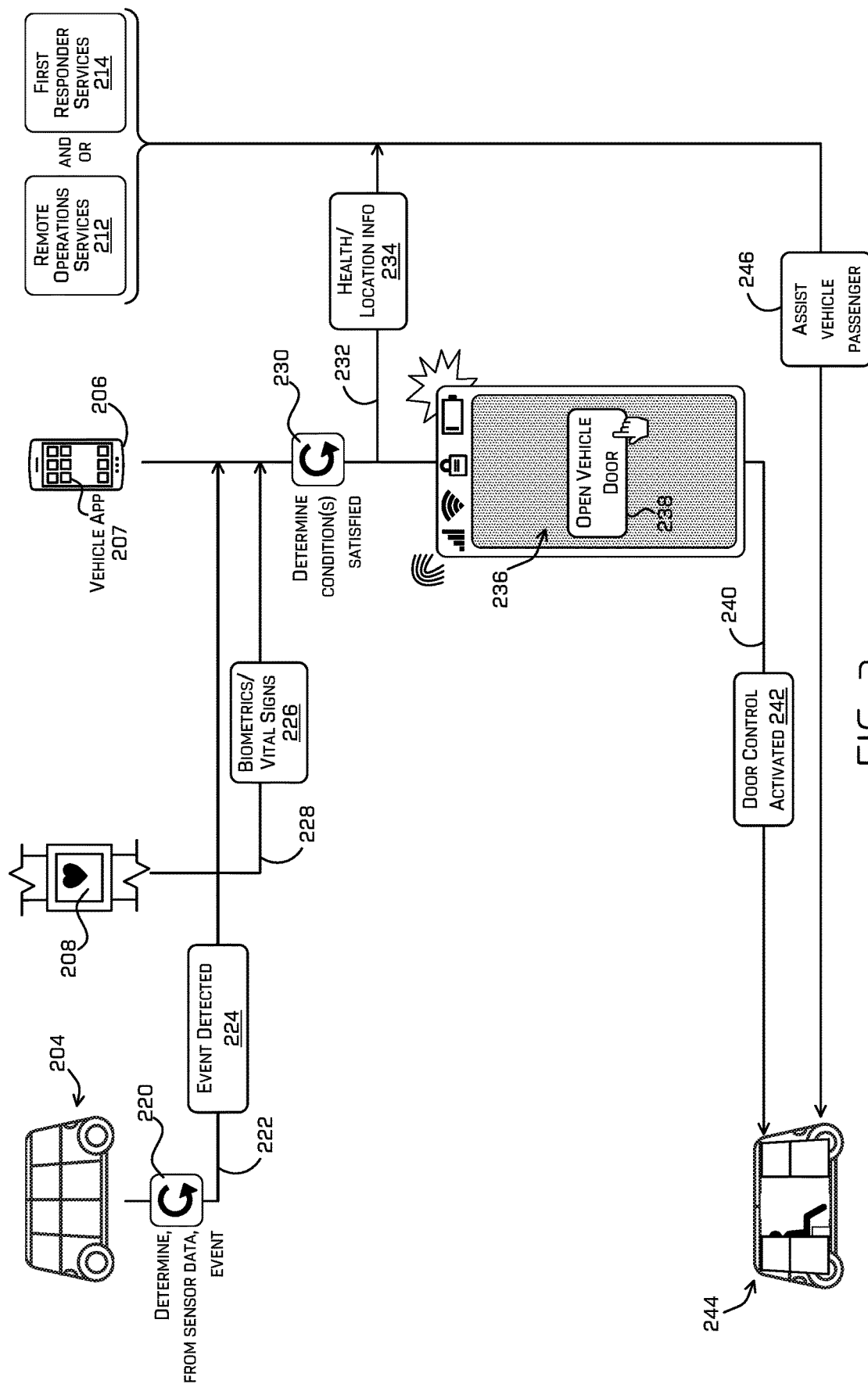
FIG. 2 depicts a diagram illustrating an example exchange of information and example operations, in accordance with one or more examples of this disclosure.

Referring now to FIG. 2, FIG. 2 depicts signal and/or communication exchange between various components in accordance with an example of the present disclosure. In addition, FIG. 2 depicts operations in a process that may be performed according to an example of the present disclosure. For example, FIG. 2 depicts a vehicle 204 (may be similar to the vehicle 104 and/or the vehicle 302), a wearable device 208 (may be similar to the wearable device 108), a vehicle app 207 (may be similar to the vehicle app 107) running on a mobile device 206 (may be similar to the mobile device 106), and a remote operations services 212 and first responder services 214 (may be similar to the remote operations services 112 and the first responder services 214). As described with respect to FIGS. 1A-1C, the mobile device 206 and the wearable device 208 may be associated with a passenger of the vehicle 204. Pursuant to an example process of the present disclosure, the vehicle 204, the wearable device 208, the mobile device 206, the vehicle app 207, the remote operations services 212, and the first responder services 214 may exchange signals and/or communications.

At operation 220, the vehicle 204 (e.g., a computing device associated with the vehicle 204) may determine, based on sensor data (e.g., airbag sensor data, motion sensor data, braking sensor data, perception system data, localization system data, steering sensor data, camera data, microphone data, etc.), an event (e.g., collision, limited vehicle operations, passenger threat, health emergency, etc.). In addition, the vehicle 204 may send 222 a communication 224 to the vehicle app 207, notifying the vehicle app 207 of the event. In some examples, the communication 224 may include an indication of a severity level associated with the event.

The vehicle app 207 may receive the communication 224, as well as other communications and/or data. For example, the vehicle app 207 may receive data 226 (e.g., biometric data, vital signs data, or other health-related information) that is transmitted 228 from the wearable device 208. Data 226 from the wearable device 208 may indicate a "current medical condition," associated with the passenger. In addition, the vehicle app 207 may receive data from another application on the mobile device 206, the other application being synced with the wearable device 208, and the data from the other application may indicate historical health information (e.g., health data captured by the wearable device 208 and provided to a synced application on the mobile device 206). In addition, the vehicle app 207 may receive or determine information associated with a state of the mobile device 206, such as whether the mobile device 206 is facing the passenger of the vehicle 204, within a pocket of a user, whether the mobile device 206 has been disposed from the passenger, and/or a location of the mobile device 206 relative to the vehicle 204 and/or the passenger of the vehicle 204. As described with respect to FIGS. 1A-1C, the wearable device 208 is one example, and in some examples, the wearable device 208 may be other types of wearable or non-wearable computing devices of the passenger.

In some examples, at operation 230, the vehicle app 207 may determine whether one or more conditions are satisfied. For example, the vehicle app 207 may determine, based on information received from the vehicle 204 and/or the wearable device 208, a severity level associated with the collision event. The severity level may be based on, among other things, whether airbags were deployed, an operational level of the vehicle 204, whether data from the wearable device 208 exceeds a threshold (e.g., vitals sign threshold or other health-data threshold), and the like. In some examples, the condition may include whether the mobile device 206 is dispossessed from the passenger and/or facing towards the passenger.

Based on the condition being satisfied, the vehicle app 207 may perform various operations. For example, the vehicle app 207 may send 232 information 234 (e.g., health information, location information, etc.) to remote operations services 212 and/or to first responder services 214. In some instances, information 234 may be sent to the remote operations services 212, which may determine whether to forward the information 234 to first responder services 214. In some examples, the information 234 may be communicated directly to first responder services 214. In addition, in some examples, based on the condition being satisfied, the vehicle app 207 may present a notification 236, such as a full-screen notification intended to help the passenger locate the mobile device 206 and provide a door control interface element 238 to operate a door of the vehicle 204. In at least some examples, the notification 236 may be presented regardless of a state of the mobile device 206, such as regardless of whether the mobile device 206 is in a locked state, has an unrelated application (or no application) open and in the foreground, and/or the vehicle app 207 is closed and/or in the background. In addition, the notification may supersede other display functionality of the mobile device 206.

In some examples, based on the door control interface element 238 being selected, the vehicle app 207 may send 240 a communication 242 to the vehicle 204 to instruct the vehicle 204 to open a vehicle door. As depicted at operation 244, the vehicle door may be opened. In addition, independent of the door operations, the remote operations services 212 and/or the first responder services 214 may assist 246 the vehicle passenger (e.g., based on the information 234), such as by communicating via the mobile device 206 and/or by providing on-site assistance at the location of the vehicle 204.

In accordance with an example, FIG. 2 depicts a variety of different operations and exchanges. Some examples of the present disclosure need not include all of elements depicted in FIG. 2. For example, the vehicle app 207 may receive information indicating a collision event, provide the notification 236, and send the message 242 indicating door control activation without necessarily receiving information from the wearable device 208 or sending information to the remote operations services 212 and/or first responder services 214. In some examples, the vehicle app 207 may present the notification 236 based on other criteria or conditions (e.g., the trigger need not be a collision event), such as a condition associated with egress of the passenger from the vehicle 204. In addition, the vehicle app 207 may receive health information (e.g., in communication 226) and forward health information (e.g., indicating a current medical emergency and/or historical or prior medical condition)

outside the context of the collision event to facilitate assistance for the vehicle passenger. In this sense, the vehicle app 207 may function as an automatic emergency button that is activated upon detecting a potential emergency based on received information (e.g., from the wearable device). FIG. 2 is described with reference to one or more of the elements shown in FIGS. 1A-IC for convenience and ease of understanding. However, the operations and/or exchanges illustrated in FIG. 2 is not limited to being performed using these elements and may be implemented using any of the other vehicles, computing devices, computing systems, and/or other elements described in this application, as well vehicles, computing devices, computing systems, and/or other elements other than those described herein. Moreover, the elements (e.g., vehicles, computing devices, computing systems, etc.) described herein are not limited to performing the method illustrated in FIG. 2.

Figure 3:
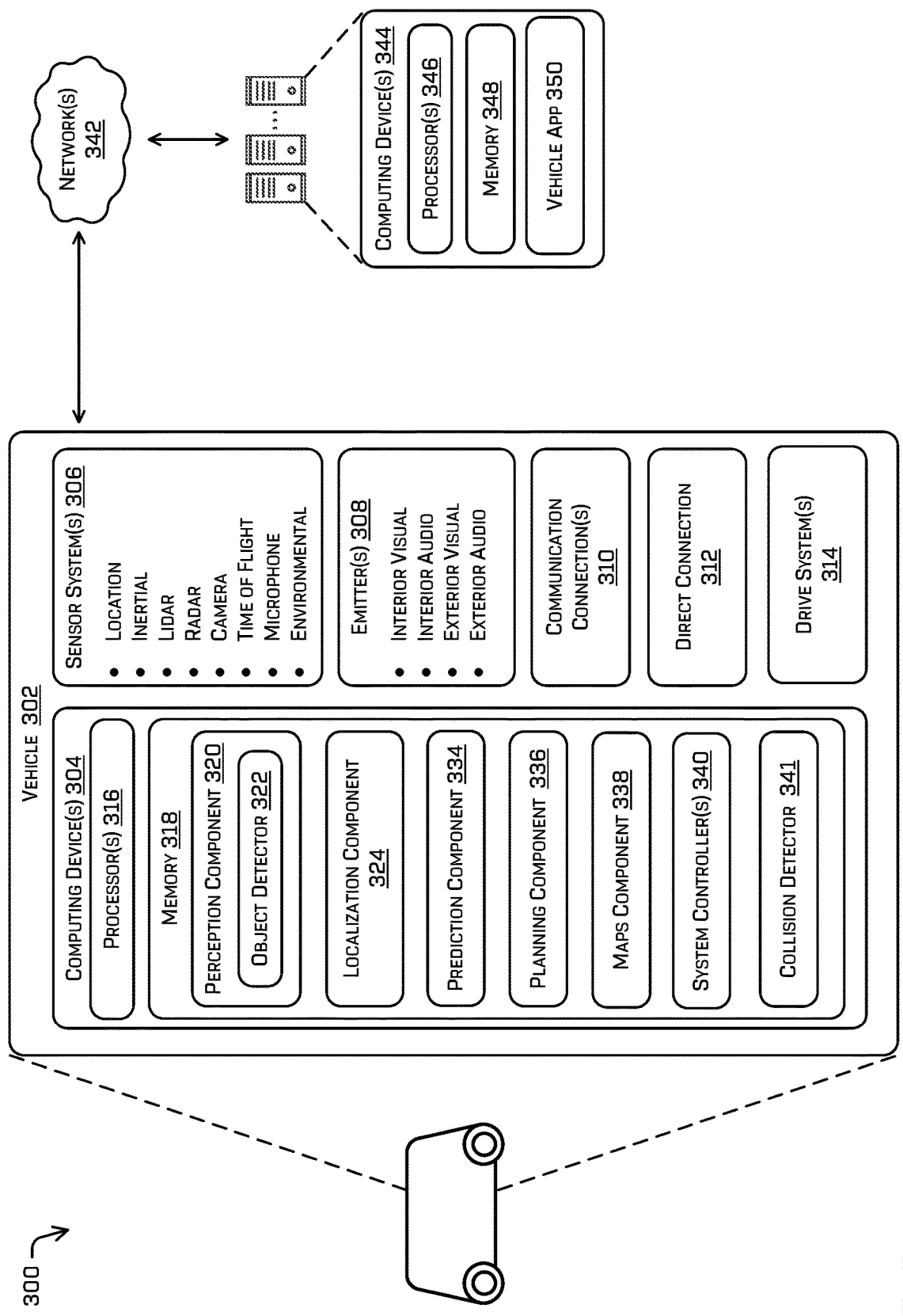
FIG. 3 is a block diagram of an example system for implementing the techniques described herein, in accordance with one or more examples of this disclosure.

Referring now to FIG. 3, FIG. 3 depicts a block diagram of an example system 300 for implementing the techniques described herein. In at least one example, the system 300 can include a vehicle 302. In the illustrated example system 300, the vehicle 302 is an autonomous vehicle; however, the vehicle 302 can be any other type of vehicle. The vehicle 302 may be the vehicle 104 depicted in FIG. 1 or the vehicle 204 in FIG. 2 and may be configured to perform various operations that send and receive information to the vehicle app 107 and/or 207.

The vehicle 302 can be a driverless vehicle, such as an autonomous vehicle configured to operate according to a Level 4 classification issued by the U.S. National Highway Traffic Safety Administration, which describes a vehicle capable of performing all safety-critical functions for the entire trip, with the driver (or occupant) not being expected to control the vehicle at any time. In such examples, because the vehicle 302 can be configured to control all functions from start to completion of the trip, including all parking functions, it may not include a driver and/or controls for driving the vehicle 302, such as a steering wheel, an acceleration pedal, and/or a brake pedal. This is merely an example, and the systems and methods described herein may be incorporated into any ground-borne, airborne, or waterborne vehicle, including those ranging from vehicles that need to be manually controlled by a driver at all times, to those that are partially or fully autonomously controlled.

The vehicle 302 can include one or more computing device(s) 304, one or more sensor system(s) 306, one or more emitter(s) 308, one or more communication connection(s) 310 (also referred to as communication devices and/or modems), at least one direct connection 312 (e.g., for physically coupling with the vehicle 302 to exchange data and/or to provide power), and one or more drive system(s) 314. The one or more sensor system(s) 306 can be configured to capture sensor data associated with an environment.

The one or more sensor system(s) 306 can include time-of-flight sensors, location sensors (e.g., GPS, compass, etc.), inertial sensors (e.g., inertial measurement units (IMUs), accelerometers, magnetometers, gyroscopes, etc.), lidar sensors, radar sensors, sonar sensors, infrared sensors, cameras (e.g., RGB, IR, intensity, depth, etc.), microphone sensors, environmental sensors (e.g., temperature sensors, humidity sensors, light sensors, pressure sensors, etc.), ultrasonic transducers, wheel encoders, chassis position sensors, etc. The one or more sensor system(s) 306 can include multiple instances of each of these or other types of sensors. For instance, the time-of-flight sensors can include individual time-of-flight sensors located at the corners, front, back, sides, and/or top of the vehicle 302. As another example, the camera sensors can include multiple cameras disposed at various locations about the exterior and/or interior of the vehicle 302. As another example, the sensor system(s) 306 may include one or more sensors for detecting a collision. The one or more sensor system(s) 306 can provide input to the computing device 304.

The vehicle 302 can also include one or more emitter(s) 308 for emitting light and/or sound. The one or more emitter(s) 308 in this example include interior audio and visual emitters to communicate with passengers of the vehicle 302. By way of example and not limitation, interior emitters can include speakers, lights, signs, display screens, touch screens, haptic emitters (e.g., vibration and/or force feedback), mechanical actuators (e.g., seatbelt tensioners, seat positioners, headrest positioners, etc.), and the like. The one or more emitter(s) 308 in this example also include exterior emitters. By way of example and not limitation, the exterior emitters in this example include lights to signal a direction of travel or other indicator of vehicle action (e.g., indicator lights, signs, light arrays, etc.), and one or more audio emitters (e.g., speakers, speaker arrays, horns, etc.) to audibly communicate with pedestrians or other nearby vehicles, one or more of which may comprise acoustic beam steering technology.

The vehicle 302 can also include one or more communication connection(s) 310 that enable communication between the vehicle 302 and one or more other local or remote computing device(s) (e.g., mobile device 106/206, wearable device 108/208, charging station, a remote teleoperation computing device, first responder computing device, etc.) or remote services. For instance, the one or more communication connection(s) 310 can facilitate communication with other local computing device(s) on the vehicle 302 and/or the one or more drive system(s) 314. Also, the one or more communication connection(s) 310 can allow the vehicle 302 to communicate with other nearby computing device(s) (e.g., other nearby vehicles, traffic signals, etc.).

The one or more communications connection(s) 310 can include physical and/or logical interfaces for connecting the computing device 304 to another computing device or one or more external networks 342 (e.g., the Internet). For example, the one or more communications connection(s) 310 can enable Wi-Fi-based communication such as via frequencies defined by the IEEE 802.11 standards, short range wireless frequencies such as Bluetooth, cellular communication (e.g., 2G, 3G, 3G, 3G LTE, 3G, etc.), satellite communication, dedicated short-range communications (DSRC), or any suitable wired or wireless communications protocol that enables the respective computing device to interface with the other computing device(s).

In at least one example, the vehicle 302 can include one or more drive system(s) 314. In some examples, the vehicle 302 can have a single drive system 314. In at least one example, if the vehicle 302 has multiple drive systems 314, individual drive systems 314 can be positioned on opposite ends of the vehicle 302 (e.g., the front and the rear, etc.). In at least one example, the drive system(s) 314 can include one or more sensor system(s) 306 to detect conditions of the drive system(s) 314 and/or the surroundings of the vehicle 302. By way of example and not limitation, the sensor system(s) 306 can include one or more wheel encoders (e.g., rotary encoders) to sense rotation of the wheels of the drive systems, inertial sensors (e.g., inertial measurement units, accelerometers, gyroscopes, magnetometers, etc.) to measure orientation and acceleration of the drive system, cameras or other image sensors, ultrasonic sensors to acoustically detect objects in the surroundings of the drive system, lidar sensors, radar sensors, etc. Some sensors, such as the wheel encoders can be unique to the drive system(s) 314. In some cases, the sensor system(s) 306 on the drive system(s) 314 can overlap or supplement corresponding systems of the vehicle 302 (e.g., sensor system(s) 306).

The drive system(s) 314 can include many of the vehicle systems, including a high voltage battery, battery charging components, a motor to propel the vehicle, power electronics, a steering system including a steering motor and steering rack (which can be electric), a braking system including hydraulic or electric actuators, a suspension system including hydraulic and/or pneumatic components, a stability control system for distributing brake forces to mitigate loss of traction and maintain control, an HVAC system, lighting (e.g., lighting such as head/tail lights to illuminate an exterior surrounding of the vehicle), and one or more other systems (e.g., cooling system, safety systems, onboard charging system, other electrical components such as a DC/DC converter, a high voltage junction, a high voltage cable, charging system, charge port, etc.). Additionally, the drive system(s) 314 can include a drive system controller which can receive and preprocess data from the sensor system(s) 306 and to control operation of the various vehicle systems. In some examples, the drive system controller can include one or more processor(s) and memory communicatively coupled with the one or more processor(s). The memory can store one or more components to perform various functionalities of the drive system(s) 314. Furthermore, the drive system(s) 314 also include one or more communication connection(s) that enable communication by the respective drive system with one or more other local or remote computing device(s).

The computing device 304 can include one or more processor(s) 316 and memory 318 communicatively coupled with the one or more processor(s) 316. In the illustrated example, the memory 318 of the computing device 304 stores a perception component 320, a localization component 324, a prediction component 334, a planning component 336, a maps component 338, and one or more system controller(s) 340. In addition, the memory 318 may store a collision detector 341. Though depicted as residing in the memory 318 for illustrative purposes, it is contemplated that the perception component 320, the localization component 324, the prediction component 334, the planning component 336, the maps component 338, the one or more system controller(s) 340, and the collision detector 341 can additionally, or alternatively, be accessible to the computing device 304 (e.g., stored in a different component of vehicle 302) and/or be accessible to the vehicle 302 (e.g., stored remotely).

The perception component 320 can include functionality to perform object detection, segmentation, and/or classification. In some examples, the perception component 320 and/or the object detector 322 can provide processed sensor data that indicates a presence of an entity that is proximate to the vehicle 302 and/or a classification of the entity as an entity type (e.g., car, pedestrian, cyclist, building, tree, road surface, curb, sidewalk, unknown, etc.). In additional and/or alternative examples, the perception component 320 can provide processed sensor data that indicates one or more characteristics associated with a detected entity and/or the environment in which the entity is positioned. In some examples, characteristics associated with an entity can include, but are not limited to, an x-position (global position), a y-position (global position), a z-position (global position), an orientation, an entity type (e.g., a classification), a velocity of the entity, an extent of the entity (size), etc. Characteristics associated with the environment can include, but are not limited to, a presence of another entity in the environment, a state of another entity in the environment, a time of day, a day of a week, a season, a weather condition, an indication of darkness/light, etc.

Further, the perception component 320 can include functionality to store perception data generated by the perception component 320. In some instances, the perception component 320 can determine a track corresponding to an object that has been classified as an object type. For purposes of illustration only, the perception component 320, using sensor system(s) 306 can capture one or more images of an environment, which may be used to determine information about an environment.

The stored perception data can, in some examples, include fused perception data captured by the vehicle. Fused perception data can include a fusion or other combination of sensor data from sensor system(s) 306, such as image sensors, lidar sensors, radar sensors, time-of-flight sensors, sonar sensors, global positioning system sensors, internal sensors, and/or any combination of these. The stored perception data can additionally or alternatively include classification data including semantic classifications of objects (e.g., pedestrians, vehicles, buildings, road surfaces, etc.) represented in the sensor data. The stored perception data can additionally or alternatively include track data (positions, orientations, sensor features, etc.) corresponding to motion of objects classified as dynamic objects through the environment. The track data can include multiple tracks of multiple different objects over time. This track data can be mined to identify images of certain types of objects (e.g., pedestrians, animals, etc.) at times when the object is stationary (e.g., standing still) or moving (e.g., walking, running, etc.). In this example, the computing device determines a track corresponding to a pedestrian.

In general, the object detector 322 can detect (among other things) semantic objects represented by sensor data. In some examples, the object detector 322 can identify such semantic objects and can determine a two-dimensional or a three-dimensional bounding box associated with the object. The object detector 322 can determine additional information such as a location, orientation, pose, and/or size (e.g., length, width, height, etc.) associated with the object. The object detector 322 can send data to other components of the system 300 for localization and/or determining calibration information, as discussed herein.

The localization component 324 can include functionality to receive data from the sensor system(s) 306 and/or other components to determine a position of the vehicle 302. For example, the localization component 324 can include and/or request/receive a three-dimensional map of an environment and can continuously determine a location of the autonomous vehicle within the map. In some instances, the localization component 324 can use SLAM (simultaneous localization and mapping) or CLAMS (calibration, localization and mapping, simultaneously) to receive time-of-flight data, image data, lidar data, radar data, sonar data, IMU data, GPS data, wheel encoder data, or any combination thereof, and the like to accurately determine a location of the autonomous vehicle. In some instances, the localization component 324 can provide data to various components of the vehicle 302 to determine an initial position of an autonomous vehicle for generating a trajectory or for initial calibration.

The prediction component 334 can generate one or more probability maps representing prediction probabilities of possible locations of one or more objects in an environment. For example, the prediction component 334 can generate one or more probability maps for vehicles, pedestrians, animals, and the like within a threshold distance from the vehicle 302. In some instances, the prediction component 334 can measure a track of an object and generate a discretized prediction probability map, a heat map, a probability distribution, a discretized probability distribution, and/or a trajectory for the object based on observed and predicted behavior. In some instances, the one or more probability maps can represent an intent of the one or more objects in the environment.

The planning component 336 can determine a path for the vehicle 302 to follow to traverse through an environment. For example, the planning component 336 can determine various routes and paths and various levels of detail. In some instances, the planning component 336 can determine a route to travel from a first location (e.g., a current location) to a second location (e.g., a target location). For the purpose of this discussion, a route can be a sequence of waypoints for traveling between two locations. As non-limiting examples, waypoints include streets, intersections, global positioning system (GPS) coordinates, etc. Further, the planning component 336 can generate an instruction for guiding the autonomous vehicle along at least a portion of the route from the first location to the second location. In at least one example, the planning component 336 can determine how to guide the autonomous vehicle from a first waypoint in the sequence of waypoints to a second waypoint in the sequence of waypoints. In some examples, the instruction can be a path, or a portion of a path. In some examples, multiple paths can be substantially simultaneously generated (i.e., within technical tolerances) in accordance with a receding horizon technique. A single path of the multiple paths in a receding data horizon having the highest confidence level may be selected to operate the vehicle.

In other examples, the planning component 336 can alternatively, or additionally, use data from the perception component 320 and/or the prediction component 334 to determine a path for the vehicle 302 to follow to traverse through an environment. For example, the planning component 336 can receive data from the perception component 320 and/or the prediction component 334 regarding objects associated with an environment. Using this data, the planning component 336 can determine a route to travel from a first location (e.g., a current location) to a second location (e.g., a target location) to avoid objects in an environment. In at least some examples, such a planning component 336 may determine there is no such collision free path and, in turn, provide a path which brings vehicle 302 to a safe stop avoiding all collisions and/or otherwise mitigating damage. In some examples, the planning component 336 may determine, based on information from a wearable device, a trajectory. For example, the planning component 336 may modify a trajectory to include a new destination (e.g., first responder, healthcare facility, emergency contact, emergency stop, etc.) if the information from the wearable device indicates a health emergency.

The memory 318 can further include one or more maps associated with a maps component 338 that can be used by the vehicle 302 to navigate within the environment. For the purpose of this discussion, a map can be any number of data structures modeled in two dimensions, three dimensions, or N-dimensions that are capable of providing information about an environment, such as, but not limited to, topologies (such as intersections), streets, mountain ranges, roads, terrain, and the environment in general. A map can further include an object identifier, an object classification, a three-dimensional location, covariance data (e.g., represented in image data or a multi-resolution voxel space), and the like. In some instances, a map can include, but is not limited to: texture information (e.g., color information (e.g., RGB color information, Lab color information, HSV/HSL color information), and the like), intensity information (e.g., LIDAR information, RADAR information, and the like); spatial information (e.g., image data projected onto a mesh, individual "surfels" (e.g., polygons associated with individual color and/or intensity)), reflectivity information (e.g., specularity information, retroreflectivity information, BRDF information, BSSRDF information, and the like). In one example, a map can include a three-dimensional mesh of the environment. In some instances, the map can be stored in a tiled format, such that individual tiles of the map represent a discrete portion of an environment, and can be loaded into working memory as needed, as discussed herein. In at least one example, the one or more maps from the map(s) component 338 can include at least one map (e.g., images and/or a mesh). In some examples, the vehicle 302 can be controlled based at least in part on the map(s) component 338. That is, the map(s) component 338 can be used in connection with the perception component 320 (and subcomponents), the localization component 324 (and subcomponents), the prediction component 334, and/or the planning component 336 to determine a location of the vehicle 302, identify objects in an environment, generate prediction probabilit(ies) associated with objects and/or the vehicle 302, and/or generate routes and/or trajectories to navigate within an environment.

In at least one example, the computing device 304 can include one or more system controller(s) 340, which can be configured to control steering, propulsion, braking, safety, emitters, communication, and other systems of the vehicle 302. These system controller(s) 340 can communicate with and/or control corresponding systems of the drive system(s) 314 and/or other components of the vehicle 302, which may be configured to operate in accordance with a path provided from the planning component 336.

The computing device 304 can also, in some examples, include a collision detector 341, which may detect a collision event. In addition, the collision detector 341 may determine a severity level associated with the collision event. Information indicating the collision and/or the severity level may be communicated to other devices, such as the drive system(s) 314, as well as other local and/or remote devices.

The vehicle 302 can connect to computing device(s) 344 via network 342, and the computing device(s) 344 may include one or more processor(s) 346 and memory 348 communicatively coupled with the one or more processor(s) 346. In at least one instance, the one or more processor(s) 346 can be similar to the processor(s) 316 and the memory 348 can be similar to the memory 318. In at least one example, the computing device(s) 344 may include a computing device associated with remote operations services and/or first responder services. In at least some examples, the computing device(s) 344 may include a passenger device, such as a mobile device (e.g., 106 or 206) and/or a wearable device (e.g., 108 or 208). In some examples, the computing device(s) 344 may include an instance of a vehicle app 350, such as the vehicle app 107 and/or 207.

The processor(s) 316 of the computing device 304 and the processor(s) 346 of the computing device(s) 344 can be any suitable processor capable of executing instructions to process data and perform operations as described herein. By way of example and not limitation, the processor(s) 316 and 346 can comprise one or more Central Processing Units (CPUs), Graphics Processing Units (GPUs), or any other device or portion of a device that processes electronic data to transform that electronic data into other electronic data that can be stored in registers and/or memory. In some examples, integrated circuits (e.g., ASICs, etc.), gate arrays (e.g., FPGAs, etc.), and other hardware devices can also be considered processors in so far as they are configured to implement encoded instructions.

The memory 318 computing device 304 and the memory 348 of the computing device(s) 344 are examples of non-transitory computer-readable media. The memory 318 and 348 can store an operating system and one or more software applications, instructions, programs, and/or data to implement the methods described herein and the functions attributed to the various systems. In various implementations, the memory 318 and 348 can be implemented using any suitable memory technology, such as static random access memory (SRAM), synchronous dynamic RAM (SDRAM), nonvolatile/Flash-type memory, or any other type of memory capable of storing information. The architectures, systems, and individual elements described herein can include many other logical, programmatic, and physical components, of which those shown in the accompanying figures are merely examples that are related to the discussion herein.

In some instances, aspects of some or all of the components discussed herein can include any models, algorithms, and/or machine-learning algorithms. For example, in some instances, the components in the memory 318 and 348 can be implemented as a neural network. In some examples a machine learned model could be trained for object detection or trajectory planning for parking in position to align coils. In some examples, a model could be trained to detect a collision, determine a collision severity, detect a health anomaly, and the like.

As described herein, an exemplary neural network is a biologically inspired algorithm which passes input data through a series of connected layers to produce an output. Any layers in a neural network can also comprise another neural network, or can comprise any number of layers (whether convolutional or not). As can be understood in the context of this disclosure, a neural network can utilize machine learning, which can refer to a broad class of such algorithms in which an output is generated based on learned parameters.

Although discussed in the context of neural networks, any type of machine learning can be used consistent with this disclosure. For example, machine learning or machine-learned algorithms can include, but are not limited to, regression algorithms (e.g., ordinary least squares regression (OLSR), linear regression, logistic regression, stepwise regression, multivariate adaptive regression splines (MARS), locally estimated scatterplot smoothing (LOESS)), instance-based algorithms (e.g., ridge regression, least absolute shrinkage and selection operator (LASSO), elastic net, least-angle regression (LARS)), decisions tree algorithms (e.g., classification and regression tree (CART), iterative dichotomiser 3 (ID3), Chi-squared automatic interaction detection (CHAID), decision stump, conditional decision trees), Bayesian algorithms (e.g., naïve Bayes, Gaussian naïve Bayes, multinomial naïve Bayes, average one-dependence estimators (AODE), Bayesian belief network (BNN), Bayesian networks), clustering algorithms (e.g., k-means, k-medians, expectation maximization (EM), hierarchical clustering), association rule learning algorithms (e.g., perceptron, back-propagation, hopfield network, Radial Basis Function Network (RBFN)), deep learning algorithms (e.g., Deep Boltzmann Machine (DBM), Deep Belief Networks (DBN), Convolutional Neural Network (CNN), Stacked Auto-Encoders), Dimensionality Reduction Algorithms (e.g., Principal Component Analysis (PCA), Principal Component Regression (PCR), Partial Least Squares Regression (PLSR), Sammon Mapping, Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA)), Ensemble Algorithms (e.g., Boosting, Bootstrapped Aggregation (Bagging), AdaBoost, Stacked Generalization (blending), Gradient Boosting Machines (GBM), Gradient Boosted Regression Trees (GBRT), Random Forest), SVM (support vector machine), supervised learning, unsupervised learning, semi-supervised learning, etc.

Additional examples of architectures include neural networks such as ResNet30, ResNet101, VGG, DenseNet, PointNet, and the like.

Figure 4:
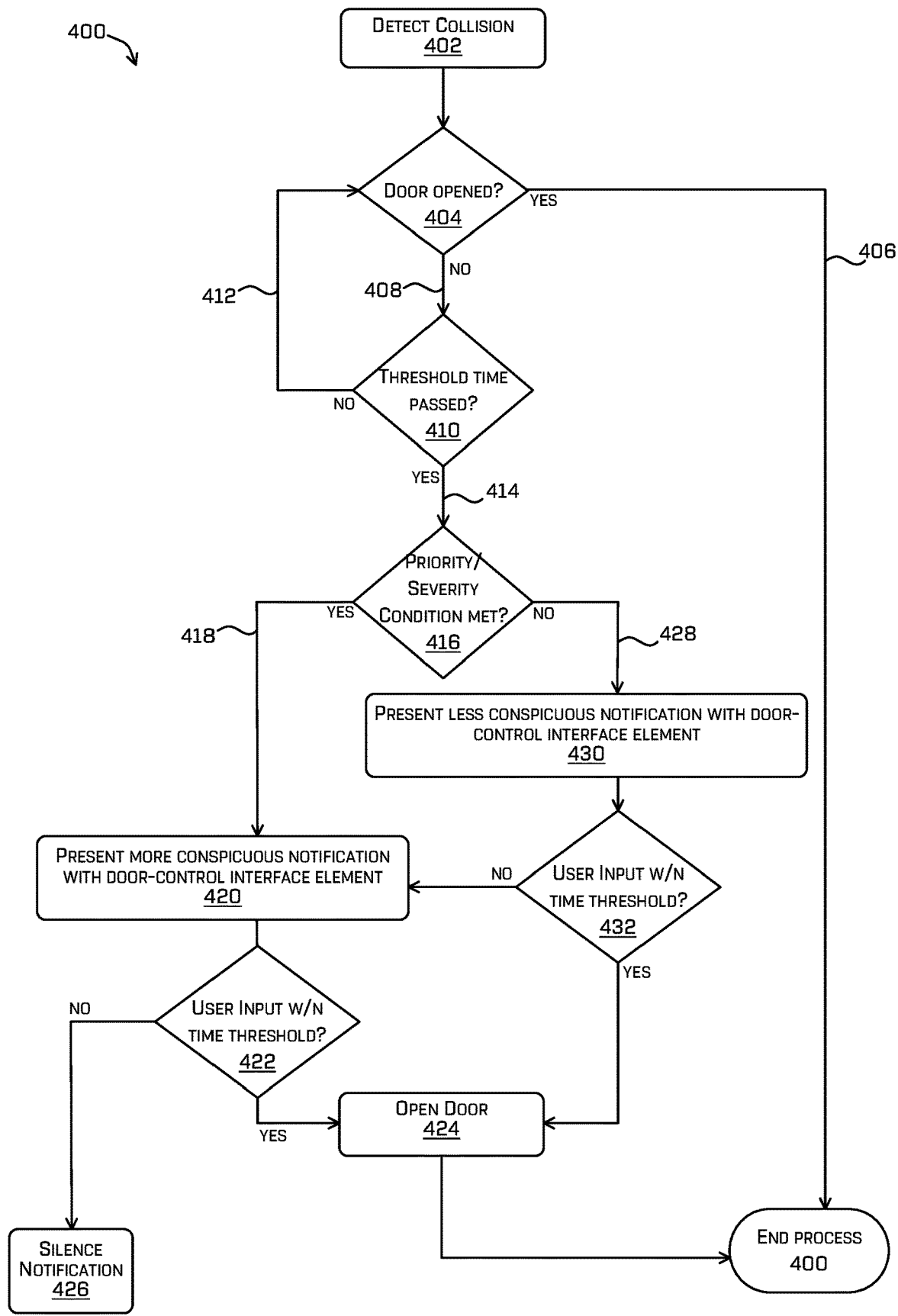
FIG. 4 depicts a flow diagram associated with a method for, based on a collision, presenting a notification, in accordance with one or more examples of this disclosure.

Referring to FIG. 4, FIG. 4 includes a flowchart showing an example related presenting, based on a collision, a notification via a mobile device of a passenger. The method illustrated in FIG. 4 may be described with reference to one or more of the elements shown in one or more other figures described in this specification for convenience and ease of understanding. However, the method illustrated in FIG. 4 is not limited to being performed using these elements and may be implemented using any of the other vehicles, computing devices, computing systems, and/or other elements described in this application, as well vehicles, computing devices, computing systems, and/or other elements other than those described herein. Moreover, the elements (e.g., vehicles, computing devices, computing systems, etc.) described herein are not limited to performing the method illustrated in FIG. 4.

FIG. 4 is a flowchart illustrating an example process 400 for presenting, based on a collision, a notification via a mobile device of a passenger. At step 402, the process 400 includes detecting a collision. For example, a collision may be detected based on one or more sensors of a vehicle (e.g., sensors 136 of the vehicle 104 and/or sensors of the vehicle 302) and/or one or more sensors of a mobile device (e.g., IMU of the mobile device 106).

At step 404, the process 400 includes determining whether a door of the vehicle is opened. For example, a sensor of the vehicle 104 or 302 may determine whether a door of the vehicle 104 or 302 is in an open state or a closed state. If the door of the vehicle is determined to be open, then the process 400 may proceed along the "yes" path 406, and the process 400 may end (or transition to a different process). In some examples, the step 404 may include determining whether the door control (e.g., 132 or 134) has been activated. If the door of the vehicle is determined to be closed (e.g., or a determination is made that the door control has not been activated), then the process 400 may proceed along the "no" path 408 to step 410.

The process 400 includes, at step 410, determining whether a threshold time duration has elapsed since a trigger event (e.g., time at which the collision was detected). If the threshold time duration has not elapsed, then the process 400 may proceed along the "no" path 412, and back to step 404 to determine whether the door of the vehicle is open yet. If the time duration has elapsed, then the process 400 may proceed along the "yes" path 414 to step 416.

At step 416, the process 400 includes determining whether a priority or severity condition (e.g., threshold) is met. For example, a priority or severity condition may include the mobile device being dispossessed, a level/rating associated with the collision, a state of the mobile device (e.g., in a pocket, in-hand, locked/unlocked, not facing passenger, facing passenger, etc.), motion of the mobile device (e.g., as detected by the mobile device IMUs), motion of the vehicle (e.g., as detected by the vehicle IMUs), a condition of the passenger (e.g., based on wearable device data, image data, sound data, etc.) and the like.

If at step 416, the condition is met, then the process 400 may follow the "yes" path 418, and at step 420, the process 400 includes presenting, via the mobile device, a more conspicuous notification with a door-control interface element. For example, the vehicle app 107 may present the notification 122, which includes the door control element 148 and various notification alert elements (e.g., flashing colored screen, flashing light, haptic vibration/feedback, audible alarm or feedback, etc.) to alert the passenger to the device's whereabouts. After step 420, the process 400 may include, at step 422, determining whether a user input is received within a time threshold (e.g., 2 minutes). For example, the user input may include a selection of the door-control interface element. If the user input is received within the threshold time duration, then the process 400 may proceed to step 424, which includes opening the door, and then to the end of the process 400. If at step 422 the user input is not received within the time threshold, then the process 400 may proceed to step 426, which includes silencing the notification. Step 426 may also include other operations, such as initiating a call to the remote operations services and/or first responder services (e.g., based on not receiving a response from a passenger).

Referring back to step 416, if the condition is not met, then the process 400 may follow the "no" path 428, and at step 430, the process 400 includes presenting, via the mobile device, a less conspicuous notification including a door-control interface element. For example, the vehicle app 107 may present the notification 124 (e.g., with the door-control interface element being available based on a swipe action), which may include fewer alert elements and/or alert elements having a lower intensity (e.g., as compared to the notification presented at step 420). For example, the notification presented at step 424 may not include haptic and/or audible elements and may include a visible notification with text describing the event and/or instructions for steps to follow.

At step 432, the process 400 includes determining whether a user input is received within a threshold time duration. For example, the user input may include a selection of the door-control interface element. If the user input is received within the threshold time duration, then the process 400 may proceed to step 424, which includes opening the door, and then to the end of the process 400. If at step 432 the user input is not received within the time threshold, then the process 400 may proceed to step 420, which includes presenting the more conspicuous notification (e.g., notification escalation after a time threshold with no response). From step 420, the process may proceed as described above.

FIG. 4, and the associated description above, provides an example. In some examples, one or more of the steps may be performed in a different order. In some examples, one or more of the steps may be omitted. For instance, the process may omit step 410 and proceed from step 404 to step 416. In some examples, one or more steps may be added to the process 400. For example, before presenting a door-control interface element, the process may include determining whether the mobile device has been located (e.g., turned over), determining whether an egress path is clear (e.g., based on the surrounding environment, such as traffic, smoke, etc.).

As described above with reference to FIGS. 1A, 1B, 1C, 2, 3, and 4, techniques described herein can be useful for when an event is detected, exchanging information with a vehicle passenger, such as via the passenger's mobile device and/or wearable device. Information may, in some examples, be configured to help the passenger locate the passenger device, to alert the passenger to the event, to provide instructions, and/or to provide a control interface for controlling a vehicle operation. In some examples, a notification may supersede operations of the passenger device (e.g., supersede other display functionality of the passenger device), such as by being presented even if the device is in a locked state or has an unrelated application open and in the foreground. As such, examples of the present disclosure may, when an event is detected, increase the likelihood that information is provided to the passenger(s) and to services that may be able to assist with the event. Among other things, this may enhance safety associated with the vehicle.

Some examples of the present disclosure include accessing information associated with a passenger (e.g., health data or other sensitive data). In such instances, examples comply with any applicable statutes, regulations, or other dictums (e.g., Health Insurance Portability and Accountability Act) related to access, storage, privacy, and the like. For instance, prior to storing or sharing any personal information, users can be provided with information regarding their rights and responsibilities, information regarding how their data will be stored and shared, may be given the option to opt in to any services that store and/or share personal information.

EXAMPLE CLAUSES

A: A method comprising: receiving, by an application executed via a mobile device and from a wearable device, data indicating vital signs information associated with a passenger in a vehicle; determining, based on the data, a condition is satisfied, the condition indicating a current medical emergency event associated with the passenger; sending, based on the condition being satisfied and via the mobile device, a request to a first remote computing device to establish a communication channel between the mobile device and a second remote computing device, the second remote computing device being associated with remote operations services; and sending, via the communication channel and to the second remote computing device, the data indicating the vital signs information, which is sent to a third remote computing device associated with first responder services.

B: The method of paragraph A further comprising: determining location data indicating a location of one or more of the vehicle or the mobile device, wherein the location data is sent to the third remote computing device.

C: The method of either paragraph A or B further comprising: establishing, with the vehicle or the mobile device, a three-way communication channel with the remote operations services and the first responder services.

D: The method of any one of paragraphs A-C further comprising: sending a request to modify, based on the current medical emergency event, a trajectory of the vehicle to include an updated destination, wherein the updated destination includes one or more of an emergency-stop location, a first-responder location, or a healthcare-facility location.

E: The method of any one of paragraphs A-D further comprising: providing, to a second mobile device of a second passenger of the vehicle, an alert indicating the current medical emergency event.

F: A method comprising: receiving, by an application executed via a mobile device, data indicating medical information associated with a passenger in a vehicle; determining a condition is satisfied, the condition indicating an event associated with the passenger or the vehicle: establishing, based on the condition being satisfied, a communication channel between the mobile device and a remote computing device, the remote computing device being associated with remote operations services or first responder services; and sending, via the communication channel and to the remote computing device, the data indicating the medical information.

G: The method of paragraph F, wherein the medical information includes one or more of emergency contact information, medical history, or vital signs information.

H: The method of paragraph G, wherein: the condition includes a health anomaly; and determining the condition is satisfied includes determining the vital signs information exceeds a vitals threshold.

I: The method of paragraph H, further comprising: modifying, based on the health anomaly, a trajectory of the vehicle to include an updated destination, wherein the updated destination includes one or more of an emergency-stop location, a first-responder location, or a healthcare-facility location.

J: The method of any one of paragraphs F-I further comprising: presenting, via the mobile device, a notification associated with the event, wherein a format of the notification is based at least in part on the medical information.

K: The method of any one of paragraphs F-J, wherein: the remote computing device is associated with remote operations services; and the method further comprises transmitting, by the remote computing device, the medical information to a second computing device associated with first responder services.

L: The method of paragraph K further comprising: determining a location of the vehicle; and transmitting the location to the second computing device.

M: The method of any one of paragraphs F-L, wherein: the condition includes detection of a collision associated with the vehicle; and determining the condition is satisfied includes receiving, from a sensor of the vehicle, data indicating the collision associated with the vehicle.

N: A method comprising: receiving data indicating medical information associated with a passenger in a vehicle, wherein the data is captured by a device associated with the passenger; determining a condition is satisfied, the condition indicating an event associated with the passenger or the vehicle; establishing, based on the condition being satisfied, a communication channel with a remote computing device, the remote computing device being associated with one or more of remote operations services or first responder services; and sending, via the communication channel and to the remote computing device, the data indicating the medical information.

O: The method of paragraph N, wherein: the condition includes a health anomaly; and determining the condition is satisfied includes determining the medical information exceeds a vitals sign threshold.

P: The method of paragraph O further comprising, modifying, based on the health anomaly, a trajectory of the vehicle to include an updated destination, wherein the updated destination includes one or more of an emergency-stop location, a first-responder location, or a healthcare-facility location.

Q: The method of any one of paragraphs N-P further comprising, presenting, via a mobile device, a notification associated with the event, wherein a format of the notification is based at least in part on the medical information.

R: The method of any one of paragraphs N-Q, wherein: the remote computing device is associated with the remote operations services; and the method further comprises sending, by the remote operations services, the medical information to a second computing device associated with first responder services.

S: The method of paragraph R further comprising: determining a location of the vehicle; and sending the location in combination with the medical information to the second computing device.

T: The method of any one of paragraphs N-S, wherein: the condition includes detection of a collision associated with the vehicle; and determining the condition is satisfied includes receiving, from a sensor of the vehicle, data indicating the collision associated with the vehicle.

While the example clauses described above are described with respect to one particular implementation, it should be understood that, in the context of this document, the content of the example clauses may also be implemented via a method, device, system, a computer-readable medium, and/or another implementation. Additionally, any of examples A-T may be implemented alone or in combination with any other one or more of the examples A-T.

CONCLUSION

While one or more examples of the techniques described herein have been described, various alterations, additions, permutations and equivalents thereof are included within the scope of the techniques described herein.

In the description of examples, reference is made to the accompanying drawings that form a part hereof, which show by way of illustration specific examples of the claimed subject matter. It is to be understood that other examples can be used and that changes or alterations, such as structural changes, can be made. Such examples, changes or alterations are not necessarily departures from the scope with respect to the intended claimed subject matter. While the steps herein can be presented in a certain order, in some cases the ordering can be changed so that certain inputs are provided at different times or in a different order without changing the function of the systems and methods described. The disclosed procedures could also be executed in different orders. Additionally, various computations that are herein need not be performed in the order disclosed, and other examples using alternative orderings of the computations could be readily implemented. In addition to being reordered, the computations could also be decomposed into sub-computations with the same results.

What is claimed is:

1. A method comprising:
    receiving, by an application executed via a mobile device and from a wearable device, data indicating vital signs information associated with a passenger in a vehicle;
    determining, based on the data, a condition is satisfied, the condition indicating a current medical emergency event associated with the passenger;
    sending, based on the condition being satisfied and via the mobile device, a request to a first remote computing device to establish a communication channel between the mobile device and a second remote computing device, the second remote computing device being associated with remote operations services; and sending, via the communication channel and to the second remote computing device, the data indicating the vital signs information, which is sent to a third remote computing device associated with first responder services, wherein the third remote computing device is different than the second remote computing device.

2. The method of claim 1 further comprising:
determining location data indicating a location of one or more of the vehicle or the mobile device, wherein the location data is sent to the third remote computing device.

3. The method of claim 1 further comprising:
establishing, with the vehicle or the mobile device, a three-way communication channel with the remote operations services and the first responder services.

4. The method of claim 1 further comprising:
sending a request to modify, based on the current medical emergency event, a trajectory of the vehicle to include an updated destination, wherein the updated destination includes one or more of an emergency-stop location, a first-responder location, or a healthcare-facility location.

5. The method of claim 1 further comprising:
providing, to a second mobile device of a second passenger of the vehicle, an alert indicating the current medical emergency event.

6. A method comprising:
receiving, by an application executed via a mobile device, data indicating medical information associated with a passenger in a vehicle;
determining a condition is satisfied, the condition indicating an event associated with the passenger or the vehicle;
establishing, based on the condition being satisfied, a communication channel between the mobile device and a first remote computing device, the first remote computing device being associated with remote operations services; and
sending, via the communication channel and to the first remote computing device, the data indicating the medical information, which is sent to a second remote computing device that is different than the first remote computing device.

7. The method of claim 6, wherein the medical information includes one or more of emergency contact information, medical history, or vital signs information.

8. The method of claim 7, wherein:
the condition includes a health anomaly; and
determining the condition is satisfied includes determining the vital signs information exceeds a vitals threshold.

9. The method of claim 8, further comprising:
modifying, based on the health anomaly, a trajectory of the vehicle to include an updated destination, wherein the updated destination includes one or more of an emergency-stop location, a first-responder location, or a healthcare-facility location.

10. The method of claim 6 further comprising:
presenting, via the mobile device, a notification associated with the event, wherein a format of the notification is based at least in part on the medical information.

11. The method of claim 6, wherein the second remote computing device is associated with first responder services.

12. The method of claim 11 further comprising:
determining a location of the vehicle; and
transmitting the location to the second remote computing device.

13. The method of claim 6, wherein:
the condition includes detection of a collision associated with the vehicle; and
determining the condition is satisfied includes receiving, from a sensor of the vehicle, data indicating the collision associated with the vehicle.

14. A method comprising:
receiving data indicating medical information associated with a passenger in a vehicle, wherein the data is captured by a device associated with the passenger;
determining a condition is satisfied, the condition indicating an event associated with the passenger or the vehicle;
establishing, based on the condition being satisfied, a communication channel with a remote computing device, the remote computing device being associated with one or more of remote operations services or first responder services, wherein the remote operations services include a fleet response center that services a plurality of vehicles; and
sending, via the communication channel and to the remote computing device, the data indicating the medical information.

15. The method of claim 14, wherein:
the condition includes a health anomaly; and
determining the condition is satisfied includes determining the medical information exceeds a vitals sign threshold.

16. The method of claim 15 further comprising, modifying, based on the health anomaly, a trajectory of the vehicle to include an updated destination, wherein the updated destination includes one or more of an emergency-stop location, a first-responder location, or a healthcare-facility location.

17. The method of claim 14 further comprising, presenting, via a mobile device, a notification associated with the event, wherein a format of the notification is based at least in part on the medical information.

18. The method of claim 14, wherein:
the remote computing device is associated with the remote operations services; and
the method further comprises sending, by the remote operations services, the medical information to a second computing device associated with first responder services.

19. The method of claim 18 further comprising:
determining a location of the vehicle; and
sending the location in combination with the medical information to the second computing device.

20. The method of claim 14, wherein:
the condition includes detection of a collision associated with the vehicle; and
determining the condition is satisfied includes receiving, from a sensor of the vehicle, data indicating the collision associated with the vehicle.

* * * * *